US011083708B2

(12) United States Patent
Bier et al.

(10) Patent No.: US 11,083,708 B2
(45) Date of Patent: Aug. 10, 2021

(54) PHARMACOLOGICAL RESTORATION OF EPITHELIAL OR ENDOTHELIAL BARRIER INTEGRITY BY AGENTS BLOCKING EPAC/RAP1 SIGNALING

(71) Applicant: The Regents of the University of California, Oakland, CA (US)

(72) Inventors: Ethan Bier, San Diego, CA (US); Annabel Guichard, La Jolla, CA (US); Victor Nizet, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/549,552

(22) Filed: Aug. 23, 2019

(65) Prior Publication Data

US 2020/0061027 A1    Feb. 27, 2020

Related U.S. Application Data

(60) Provisional application No. 62/722,224, filed on Aug. 24, 2018.

(51) Int. Cl.
*A61K 31/42* (2006.01)
*A61K 31/277* (2006.01)
*A61K 31/4196* (2006.01)
*A61K 9/00* (2006.01)

(52) U.S. Cl.
CPC ............ *A61K 31/42* (2013.01); *A61K 9/0019* (2013.01); *A61K 9/0095* (2013.01); *A61K 31/277* (2013.01); *A61K 31/4196* (2013.01)

(58) Field of Classification Search
CPC ............................ A61K 31/42; A61K 31/277
See application file for complete search history.

(56) References Cited

PUBLICATIONS

Tao et al. Journal of Virology, 2014, vol. 88, No. 7, pp. 3902-3910.*

\* cited by examiner

*Primary Examiner* — Samira J Jean-Louis
(74) *Attorney, Agent, or Firm* — Eversheds Sutherland (US) LLP

(57) ABSTRACT

Methods and pharmaceutical compositions for treating diseases characterized by compromised epithelial or endothelial barrier integrity are provided. The pharmaceutical compositions include an effective amount a Epac/Rap1 signaling inhibitor. The methods include administering to a patient suffering from a disease characterized by compromised epithelial or endothelial barrier integrity a therapeutically effective amount of a Epac/Rap1 signaling inhibitor, such as ESI-09, SecinH3, Slit, or AG1024.

16 Claims, 16 Drawing Sheets

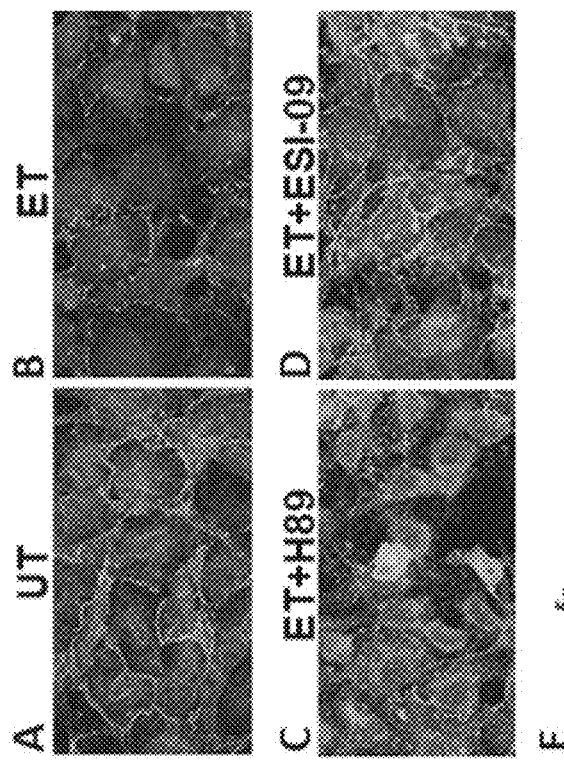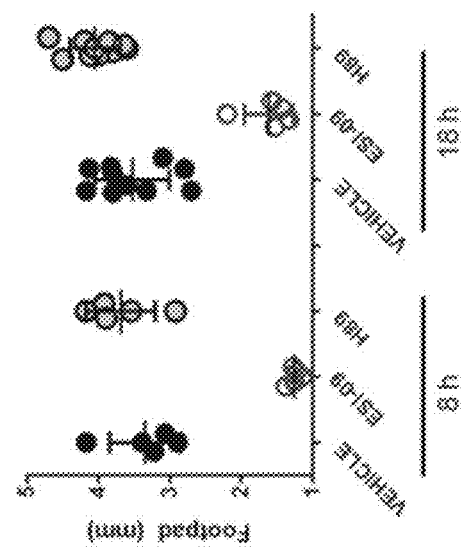
Figures 16A-16E

PHARMACOLOGICAL RESTORATION OF EPITHELIAL OR ENDOTHELIAL BARRIER INTEGRITY BY AGENTS BLOCKING EPAC/RAP1 SIGNALING

CROSS REFERENCE TO RELATED APPLICATIONS

This application claims the priority benefit of U.S. Provisional Application No. 62/722,224, filed Aug. 24, 2018, which application is incorporated herein by reference in its entirety.

STATEMENT OF GOVERNMENT INTEREST

The invention was made with government support under Grant No. R01 AI110713 awarded by the National Institutes of Health (NIH). The government has certain rights in the invention.

FIELD OF THE INVENTION

The present disclosure relates to Epac/Rap1 signaling inhibitor compositions and methods of using the same to treat diseases characterized by compromised epithelial or endothelial barrier integrity.

BACKGROUND OF THE INVENTION

Bacterial pathogens enhance infectivity by secreting toxins that deregulate immune signaling pathways or disrupt host cellular barriers. Interestingly, a set of toxins produced by diverse bacterial species act by distinct mechanisms to dramatically increase the intracellular concentration of cAMP. This striking evolutionary convergence suggests that overproduction of this second messenger represents a successful strategy to promote growth and dissemination of infectious agents, as well as disease symptoms [1]. These toxins include adenylate cyclases (AC), such as Edema Factor (EF) from *Bacillus anthracis* (B.a), CyaA from *Bordetella pertussis*, and ExoY from *Pseudomonas aeruginosa*. Other toxins modify host proteins to induce cAMP production by the cellular machinery. For example, the *Vibrio cholerae* (V.c) Cholera toxin (Ctx) and the related heat-labile toxin from Enterotoxigenic *Escherichia coli* ADP ribosylate the a subunit of trimeric G proteins to stimulate cAMP synthesis, while Pertussis toxin (Ptx) ADP ribosylates and inactivates Gi subunits that normally inhibit endogenous ACs (reviewed in [2]).

*Bacillus anthracis* (B.a.), the etiological agent of anthrax, produces two A-subunit toxins EF and Lethal Factor (LF), which are secreted together with a shared B-subunit protective antigen (PA) and then assemble to form Edema Toxin (ET) and Lethal Toxin (LT), respectively [3]. ET and LT can enter a wide array of mammalian cells expressing either of two related surface receptors, CMG2 or TEM8, whereupon the toxins are internalized and the enzymatic A-subunits are released into the cytoplasm [4]. LF is a zinc metalloprotease that cleaves and inactivates mitogen activated protein kinases kinases (MAPKKs or MEKs) to block MAPK signaling pathways [5], while EF is a Calmodulin-dependent AC estimated to be a thousand times more potent than its mammalian counterparts in raising intracellular cAMP concentrations [6]. During the early stages of anthrax infection, LT and ET inhibit the innate immune response, affecting host cell viability, chemotaxis and phagocytosis and deregulating cytokine production by macrophages, dendritic cells, and lymphocytes, ultimately promoting bacterial growth and dissemination throughout the host [7,8]. In late fulminant stages of the disease, increasing amounts of ET and LT [9] are released into the bloodstream causing edema, bleeding and hemorrhagic lesions (EF), atypical collapse of the cardiovascular system (LF), often culminating in cardiac arrest and death [10,11].

Molecular pathways altered by the concerted effects of EF and LF have been analyzed in transgenic *Drosophila* models wherein expression of toxin-encoding sequences placed under the control of the yeast Upstream Activating Sequence (UAS) could be induced by the GAL4 trans-activator in different tissues and patterns [12]. Expression in the developing wing revealed that EF caused a phenotype very similar to that of a Dominant-Negative form of Rab11, a small GTPase of the Rab subfamily, essential for endocytic recycling [13,14]. Consistent with EF blockade of Rab11-dependent trafficking, two known cargo proteins Delta (a transmembrane ligand activating the Notch receptor) and the homophylic adhesion protein E-cadherin [15,16] failed to reach their normal destination at apical adherens junctions. In addition, Rab11 levels were severely reduced in response to EF expression in the wing disc. This activity of EF was also observed in mammalian cells where ET treatment caused a clear disruption of adherens junction (AJs) and Notch signaling in endothelial cell lines, as well as being essential for B.a. induced dye vascular effusion in vivo. To promote cargo vesicle fusion with the plasma membrane at proper apical sites, Rab11 relies on its effector Sec15, which physically binds to the GTP-bound/active form of Rab11 [11,17,18]. Sec15 is a key component of the exocyst, an octameric protein complex that triggers docking and SNARE-mediated fusion of cargo vesicles with the plasma membrane [19]. When over-expressed in various cell types, Sec15 promotes the assembly of large punctate structures [17] that also contain Rab11, Sec15, and other exocyst components. Consistent with previous observations, it was found that EF prevented the formation of such Sec15-rich punctae. Interestingly, LF led to the same inhibition of Sec15 punctae, although via a Rab11-independent mechanism, suggesting that Sec15 acts as a convergence point integrating the effects of both anthrax toxins to block exocyst-mediated trafficking and disrupt integrity of the endothelial barrier [20].

Subsequent studies indicated that cholera toxin also blocks Rab11-mediated trafficking. Ctx, which is comprised of CtxA and CtxB, is secreted in the small intestine during infection by *Vibrio cholerae* (V.c.), and enters epithelial cells through retrograde transport after binding to GM1 gangliosides. Cleavage of CtxA liberates the active CtxA1 fragment, an ADP-ribosyl transferase that constitutively activates the stimulatory subunit of trimeric G proteins. As a consequence, stimulation of endogenous ACs results in an uncontrolled production of cAMP, leading to sustained PKA activation and phosphorylation of the cystic fibrosis transmembrane conductance regulator (CFTR).

Ctx-mediated activation of this ion channel allows massive Cl-efflux of into the intestinal lumen, followed by a paracellular flow of Na+ and water, producing the life-threatening diarrhea typical of cholera patients [21,22]. As with EF, Ctx decreased Rab11 levels and activity in fly wings as well as in the midgut, causing reduced body weight, leaky guts, large fluid-filled spaces between enterocytes, and premature death. Remarkably all of these phenotypes could be significantly rescued by co-expression of Rab11 with Ctx.

Ctx also acted similarly in mammalian systems lowering Rab11 levels at intercellular junctions in mouse ileal loops and human enterocytes, altering adherens junctions and reducing Notch signaling [23]. Cumulatively, these findings support a model in which Ctx acts in part through Rab11 inhibition to increase epithelial permeability, paracellular water loss and diarrhea. These similar cellular effects of ET and Ctx are likely to contribute to the hallmark pathological features and symptoms associated with anthrax and cholera respectively [24].

Various bacterial toxins circumvent host defenses through overproduction of cAMP. In a previous study, it was shown that Edema Factor (EF), an adenylate cyclase from *Bacillus anthracis*, disrupts endocytic recycling mediated by the small GTPase Rab11. As a result, cargo proteins such as Cadherins fail to reach endothelial junctions. Similarly, Cholera toxin (an ADP-ribosyl transferase that stimulates cAMP synthesis), also blocks Rab11-dependent trafficking thereby weakening epithelial adherens junctions, and facilitating paracellular fluid flow into the intestinal lumen.

Recent anthrax outbreaks in northern Russia demonstrate the need for adjunctive therapies to alleviate symptoms in patients infected with *Bacillus anthracis*. Existing strategies to combat anthrax include vaccination and administration of antibodies directed against anthrax toxins such as Protective Antigen. Such vaccines suffer from being only partially protective and can induce side effects. As a result, only high risk individuals are typically vaccinated. Administration of anti-toxin antibodies to patients infected with anthrax is typically only effective during the earliest stages of infection, often before patients have sought medical attention, since these reagents cannot act on toxins already internalized into cells. Similarly, antibiotic treatment has a high failure rate once the patient becomes symptomatic because two toxins secreted by this pathogen—edema toxin (ET) and lethal toxin (LT)—can cause death before antibiotic treatments take effect. ET, a potent Adenylate Cyclase, severely impacts host cells and tissues through an overproduction of the ubiquitous second messenger cAMP. Rab11 was previously identified as a key factor inhibited by ET. Blockade of Rab11-dependent endocytic recycling resulted in the disruption of intercellular junctions, likely contributing to vascular effusion observed in anthrax patients. Thus, treatments are currently lacking for established anthrax and its late, life-threatening fulminant stages. Treatment with agents blocking the toxin's downstream effects within cells (i.e., the last steps in toxin action) may provide a critical tool for reversing the life-threatening symptoms of ET during fulminant stages of anthrax infection.

Current treatment of Cholera is largely confined to rehydration regimens. Although simple in principle, such intervention requires sterile water or fluids and may be ineffective when administered orally in severe life-threatening cases. Pertussis (whooping cough) is another bacterial infection in which pathology is driven by a cAMP-inducing toxin. Many other inflammatory diseases involve compromised endothelial or epithelial barrier integrity such as airway barrier disruption in asthma, atopic dermatitis such as eczema, or intestinal 'leaky gut' pathology associated with inflammatory bowel disease. There is evidence in an experimental mouse model of asthma that some of the bacterial toxin pathways may contribute to barrier dysfunction.

SUMMARY OF THE INVENTION

Anthrax Edema Toxin (ET) and Cholera Toxin (CT) are key virulence factors for the respective pathogens. These toxins disrupt vascular endothelial (ET) and intestinal epithelial (CT) barrier integrity by blocking transport of adhesion proteins such as cadherins and signaling molecules to cell-cell junctions. ET and CT act via distinct mechanisms to dramatically elevate cAMP levels in the cell. Two well-known cAMP binding proteins mediate the effects of cAMP in host cells: protein kinase A (PKA) and Epac, a guanine nucleotide exchange factor for the small GTPase Rap1.

In some embodiments, the present disclosure provides for the pharmacological restoration of epithelial or endothelial barrier integrity by agents blocking Epac/Rap1 signaling. In some embodiments, the present disclosure provides the use a small molecule inhibitor (e.g., ESI-09) of Rap1 to protect against the barrier disruptive effects of ET and CT, and to fortify endothelial and epithelial integrity in a wide variety of medical conditions in which barrier dysfunction is an important pathophysiologic feature. In some embodiments, the present disclosure provides that chemical inhibition of Epac (using e.g., ESI-09) or Arf6 (using e.g., SecinH3 or Slit), can fully reverse the effect of EF.

In embodiments, the invention provides that several agents including the soluble cell permeant Epac/Rap1 inhibitor ESI-09 can dramatically inhibit ET induced edema in vivo. In embodiments, small soluble compounds such as ESI-09 can be added to oral rehydration formulas or to IV fluids to help preserve and restore epithelial integrity in the small intestine and hasten recovery. In embodiments, the invention provides that SecinH3 (an inhibitor of the Arf6GEF ARNO) and AG1024 (an inhibitor of IGF-1Receptor which may act via inhibition of the small GTPase Rap1) can also be useful to provide pharmacological restoration of epithelial or endothelial barrier integrity by agents blocking Epac/Rap1 signaling. In some embodiments, Epac/Rap1 inhibition can be used to ameliorate tracheal epithelial barrier injury and hasten disease resolution. In some embodiments, blocking Epac/RAP1 can have broad applicability to inflammatory diseases characterized by comprised barrier integrity.

In some embodiments, compositions, and methods of using the same, are provided which reverse life-threatening symptoms in late stages of anthrax and cholera infection. In some embodiments, compositions, and methods of using the same, are provided which alleviate symptoms of whooping cough. In some embodiments, compositions, and methods of using the same, are provided which ameliorate symptoms of inflammatory diseases involving compromised endothelial or epithelial barrier integrity such as airway barrier disruption in asthma, atopic dermatitis such as eczema, or intestinal 'leaky gut' pathology associated with inflammatory bowel disease.

BRIEF DESCRIPTION OF THE DRAWINGS

FIGS. 1A-1C Wing imaginal discs expressing wild-type (wt) and mutant forms of YFP-tagged Rab11, using the strong wing GAL4 driver MS1096, and stained with a Rabbit anti-GFP antibody, reveal different sub-cellular distributions of Rab11. Insets show Z-sections of the same images. (FIG. 1A) Rab11wt, showing apical restriction. (FIG. 1B) Rab11 activated (or Rab11*), showing apical restriction plus junctional concentration, (FIG. 1C) Rab11 Dominant-Negative (or Rab11DN) showing loss of apical/junctional staining. This bipartite staining is yet more pronounced in salivary glands (FIGS. 1D-1I) where MS1096 GAL4 also drives UAS-transgene expression. (FIG. 1D) MS1096>Rab11wtYFP. (FIG. 1E) MS1096>Rab11*YFP with higher magnification in (FIG. 1H). (FIG. 1F) MS1096>Rab11*YFP+EF. EF co-expression blocks Rab11* targeting to junctions, with higher magnification in (FIG. 1I). (FIG. 1G) MS1096>Rab11DNYFP, showing that Rab11 DN does not concentrate at the junctions and alters the morphology of secretory granules. (FIGS. 1J-1M): detection of the endogenous Rab11 reveals that it collects near junctions in a punctate pattern (FIG. 1J) and (FIG. 1L), higher magnification. This preference is abrogated in EF-expressing glands (FIG. 1K) and (FIG. 1M), higher magnification. Endogenous activated Rab11 (Rab11*) accumulates next to cell junctions in salivary glands (FIG. 1N), (FIG. 1O) sagittal view, an effect that is reduced in EF expressing glands (FIG. 1P), (FIG. 1Q) sagittal view. The effect of EF on endogenous Rab11 is also visible in wing imaginal discs: (FIG. 1R) wt, (FIG. 1S) MS1096>EF. Co-labeling Rab11 and D-Ecad (FIGS. 1T-1W) reveals co-localization of Rab11 and D-Ecad at the AJs in wt salivary glands (FIG. 1T), (FIG. 1U) higher magnification. Thick arrow indicates AJs, thin arrow indicates punctate stain near the AJs. Co-localization is lost upon EF expression (FIG. 1V) in salivary glands, (FIG. 1W) higher magnification).

FIGS. 2A-2D show wing phenotypes implicating both cAMP effector pathways in cAMP-mediated inhibition of Rab11. Wings from flies of the following genotypes. (FIG. 2A) wingGAL4>PKA*. (FIG. 2B) wingGAL4>PKA*+Rab11wt (showing suppression of the PKA* phenotype by Rab11wt). (FIG. 2C) wingGAL4>Rap1* (similar to an EF phenotype, see FIG. 4A). (FIG. 2D) wingGAL4>Rap1*+PKA* (showing synergism between PKA* and Rap1*). (FIGS. 2E-2J) Rab11*YFP distribution (detected by a Rabbit anti-GFP antibody) is differentially affected by PKA* versus Rap1* in Drosophila salivary glands. (FIG. 2E) Rab11* (MS1096>Rab11*YFP glands) shows a strong preference for the intercellular junctions (see FIG. 2H for higher magnification). (FIG. 2F) PKA* induces ubiquitous redistribution of Rab11* (MS1096>Rab11*YFP+PKA* glands, see FIG. 2I for higher magnification). (FIG. 2G) Rap1* expression does not alter Rab11* targeting to the junctions, but blocks the final membrane fusion event (in MS1096>Rab11*YFP+Rap1* glands, see FIG. 2J for higher magnification). (FIGS. 2K-2M) Endogenous Rab11 (detected by a mouse anti-Rab11 antibody) is also altered by PKA* (FIG. 2L, MS1096>PKA* glands: higher levels and loss of junctional preference) and Rap1* (FIG. 2M, in MS1096>Rap1* glands: note stronger accumulation near cell junctions).

(FIG. 3A) Drosophila salivary glands stained with a Rabbit anti-GFP antibody, showing that dRip11GFP accumulates at cell-cell junctions in MS1096>dRip11-GFP larvae. (FIG. 3B) MS1096>dRip11-GFP+EF glands. Junctional staining is moderately weakened by EF. In contrast, a Dominant-Negative form of dRip11 that contains only the Rab11-binding domain fails to be targeted to junctions, in (FIG. 3C) MS1096>dRip11DN-GFP glands. (FIGS. 3D-3F) Salivary glands co-stained with a Rat anti-GFP antibody and a Rabbit anti-dRip11 antibody, showing that the co-localization between Rab11* and dRip11 detected with this antibody combination is lost upon co-expression of Rab11*YFP with EF or PKA*. (FIG. 3D) MS1096>Rab11*. (FIG. 3E) MS1096>Rab11*+EF. (FIG. 3F) MS1096>Rab11*+PKA*. (FIGS. 3G-3I) Salivary glands co-stained with a Rat anti-GFP antibody and a Guinea Pig anti-Sec15 antibody, showing that co-localization between Rab11* and Sec15 is lost upon co-expression of Rab11*YFP with EF or PKA*. (FIG. 3G) MS1096>Rab11*. (FIG. 3H) MS1096>Rab11*+EF. (FIG. 3I) MS1096>Rab11*+PKA*. (J-K) MDCK cells transfected with constructs expressing Rip11-GFP and Rab11wt-Dsred. (FIG. 3J) Untreated cells showing Rab11-Rip11 co-localization throughout the cell with higher levels of Rip11 and Rab11 at cell borders. (FIG. 3K) in cells treated with ET, Rip11 and Rab11wt no longer co-localize. While a minor component of Rip11 is still evident at cell borders, Rab11 fails to reach the cell surface.

FIGS. 4A-4E show wing phenotypes caused by expression of an activated form of Arf6 (Arf6*) closely approximate those caused by EF. (FIG. 4A) MS1096>EF. (FIG. 4B) MS1096>Arf6*. (FIG. 4C) MS1096>EF+Arf6*, showing an additive phenotype. (FIG. 4D) MS1096>Arf6wt wing, displaying a wild-type phenotype. (FIG. 4E) MS1096>EF+Arf6wt wing revealing synergy between EF and Arf6wt. (FIGS. 4F-4G) wing imaginal discs stained with an anti-Rab11 antibody, showing a dotted apical distribution of Rab11 (FIG. 4F) in wt discs. (FIG. 4G) In discs expressing Arf6* (MS1096>Arf6*), Rab11 levels are reduced, and apical restriction is lost, as observed with EF (FIG. 10J). (FIGS. 4H-4I) wing imaginal discs expressing Sec15-GFP. (FIG. 4H) High-level expression of Sec15-GFP in MS1096>Sec15-GFP discs forms large fluorescent punctae. Like EF, Arf6* expression in (FIG. 4I) MS1096>Sec15-GFP+Arf6* discs blocks formation of Sec15-GFP punctae. (FIG. 4J) D-Ecad stain in wt discs, revealing the apical network of AJs. (FIG. 4K) in MS1096>Arf6* discs, apical D-Ecad levels are severely reduced. (FIG. 4L) MS1096>Rab11*YFP gland showing Rab11* targeting to the AJs, revealed by an anti-GFP stain. (FIG. 4M) Arf6* blocks Rab11* targeting to cell junctions in MS1096>Rab11*+Arf6* glands. (FIG. 4N) Endogenous Rab11 stain of wt salivary glands. (FIG. 4O) Arf6* causes endogenous Rab11 to accumulate in the cytoplasm and diminishes its localization at junctions. (FIG. 4P) D-Ecad stain of wt salivary glands. (FIG. 4Q) Arf6* causes intense intracellular accumulation of D-Ecad in MS1096>Arf6* salivary glands.

FIGS. 5A-5E show HBMECs stained with an anti-pan-Cadherin antibody. (FIG. 5A) The pan-Cadherin stain clearly marks the cell outlines. (FIG. 5B) EF treatment results in strong reduction in AJs, as visualized by the pan-Cadherin stain. (FIG. 5C) Co-treatment with the Slit2 peptide, which prevents Arf6 activation (via induction of ArfGAP activity), restores AJs compromised by EF treatment. (FIG. 5D) Co-treatment with the Epac-specific inhibitor ESI-09 partially rescues pan-cadherin expression at AJs. (FIG. 5E) Co-treatment with the PKA-inhibitor H89 does not appreciably rescue junctional cadherin expression. (FIGS. 5F-5H) ET-induced footpad edema can be suppressed by pre-treatment with (FIG. 5F) SecinH3, a compound that indirectly suppresses the activation of Arf6 (**$p<0.0001$, *$p<0.001$), (FIG. 5G) the Epac pathway inhibitor ESI-09, but not the PKA inhibitor H89, and (FIG. 5H) AG1024, an inhibitor of IGF-1R, which may act by blocking Rap1 activity.

FIGS. 7A-7C Expression of Rab11wt in MS1096>Rab11wtYFP wing discs. (FIG. 7A) Rab11wtYFP detected with a rabbit anti-GFP antibody appears as a peppered stain near the apical surface. (FIG. 7B) D-Ecad/GFP double stain. (FIG. 7C) corresponding D-Ecad stain marking AJs. (FIGS. 7D-7F) Expression of Rab11* in MS1096>Rab11*c YFP wing discs. (FIG. 7D) Rab11*YFP detected with a rabbit anti-GFP antibody. In addition to a peppered apical stain, Rab11* shows a distinctive net-like pattern at cell borders. (FIG. 7E) D-Ecad/GFP double stain, revealing that Rab11*YFP tends to accumulate at the AJs. (FIG. 7F) corresponding D-Ecad stain.

FIGS. 8A-8C Rab11*-YFP detected with a rabbit anti-GFP antibody in salivary glands. (FIG. 8A) Rab11*-YFP selectively accumulates at the AJs in MS1096>Rab11*-YFP salivary glands. (FIG. 8B) Rab11* distribution is unchanged in MS1096>Rab11*YFP+CragRNAi glands. (FIG. 8C) Rab11*-YFP fails to accumulate at the AJs in MS1096>Rab11*-YFP+Sec15RNAi glands.

FIGS. 9A-9B Rab11*-YFP detected with a rabbit anti-GFP antibody in salivary glands. (FIG. 9A) Rab11* accumulates at cell junctions in MS1096>Rab11*-YFP salivary glands. (FIG. 9B) Ctx prevents Rab11* targeting to cell junctions in MS1096>Rab11*-YFP+Ctx salivary glands FIGS. 10A-10D Wing phenotypes of the indicated genotypes generated by expression of various transgenes with the MS1096 GAL4 driver. (FIG. 10A) wt; (FIG. 10B) EF; (FIG. 10C) RalARNAi (note EF and RalARNAi cause similar phenotypes) and (FIG. 10D) produce synergistic interaction when co-expressed. (FIGS. 10E-10H) D-Ecad stain of wing discs of the indicated genotypes, using the MS1096 GAL4 driver. FIG. 10E: wt disc. Both EF (FIG. 10F) and RalARNAi (FIG. 10G) reduce the intensity of apical D-Ecad. Co-expression of EF and RalARNAi leads to an even stronger reduction (FIG. 10H). I-L: Rab11 stain in imaginal discs of the indicated genotypes, using the MS1096 GAL4 driver. FIG. 10I: wt. While EF reduces the levels of Rab11 (FIG. 10J), RalARNAi expression increases Rab11 levels (FIG. 10K). Co-expression of EF and RalARNAi leads to a loss of Rab11, suggesting that EF acts upstream of RalA (FIG. 10L).

FIGS. 11A-11C MS1096>Rip11DN salivary glands stained with a rabbit anti-GFP antibody (FIG. 11A), a mouse anti Rab11 antibody (FIG. 11B), and both antibodies (FIG. 11C), showing that Rab11 and Rip11DN co-localize in punctate vesicles. FIGS. 11D-11F: MS1096>Rip11DN+EF salivary glands stained with a rabbit anti-GFP antibody (FIG. 11D), a mouse anti-Rab11 antibody (FIG. 11E), and both antibodies (FIG. 11F), showing that Rab11 and Rip11DN still co-localize in EF-expressing glands. However, EF alters the distribution of both proteins, transforming small punctate staining into a ring-shaped halo surrounding secretory vesicles.

FIGS. 12A-12C: HBMECs, untreated. FIGS. 12D-12F: HBMECs treated with ET for 6 hrs. Co-localization of Rab11*-Sec15 (FIG. 12B and FIG. 12E) and Rab11*-Rip11 (FIG. 12C and FIG. 12F) can be visualized following transfection of cells with Sec15-GFP. High level expression of Sec15-GFP, and staining with an anti-Rab11* antibody (FIG. 12A) reveals a high degree of Sec15-Rab11* co-localization (FIG. 12B). In ET-treated cells, this co-localization is severely reduced (FIG. 12E). Rip11 stain, reveals Rab11*-Rip11 co-localization (FIG. 12C), which is also abrogated by ET (FIG. 12F).

FIGS. 14A-14C: Evans Blue dye effusion in inverted dermis from mice injected with PBS (FIG. 14A), wt B.a (FIG. 14B), and AEF-B.a. (FIG. 14C), showing induction of EF-dependent edema. FIGS. 14D-14F: paraffin-embedded skins from mice in a parallel experiment, stained with a rabbit anti-Rab11 antibody. Blood vessels show luminal accumulation of Rab11 in control blood vessels surrounding PBS injection (FIG. 14D), which is compromised in vessels surrounding wt-B.a injection (FIG. 14E), but not in vessels surrounding the site AEF-B.a injection (FIG. 14F).

FIGS. 15A-15F: Drosophila wings from individuals expressing combinations of EF, an RNA interference (RNAi) construct directed against Epac, or activated forms of Rap1 (Rap1*) or PKA (PKA*). FIGS. 15G-15O: Expression of Rab11 (FIGS. 15G-15I), Sec15-GFP (FIGS. 15J-15L) and Delta (FIGS. 15M-15O) in Drosophila wing discs from wild-type individuals (wt: FIGS. 15G, 15J, 15M) or those expressing Rap1* (FIGS. 15H, 15K, 15N) or PKA* (FIGS. 15I, 15L, 15O).

FIGS. 16A-16E shows cellular and in vivo evidence that Epac inhibition can protect against the effects of edema toxin. FIGS. 16A-16D: Human Brain Microvascular Endothelial Cells (HBMECs) treated with edema toxin (ET) with or without inhibitors of PKA (H89) or Epac (ESI-09). FIG. 16E: ESI-09 but not H89 injected systemically in mice can reverse the footpad swelling resulting from ET injection into footpads at both early (8 h) and late (18 h) times. ESI-09 can partially restore junctional barrier integrity in cultures of human vascular endothelial cells.

DETAILED DESCRIPTION OF THE INVENTION

Figures 1A, 1W:
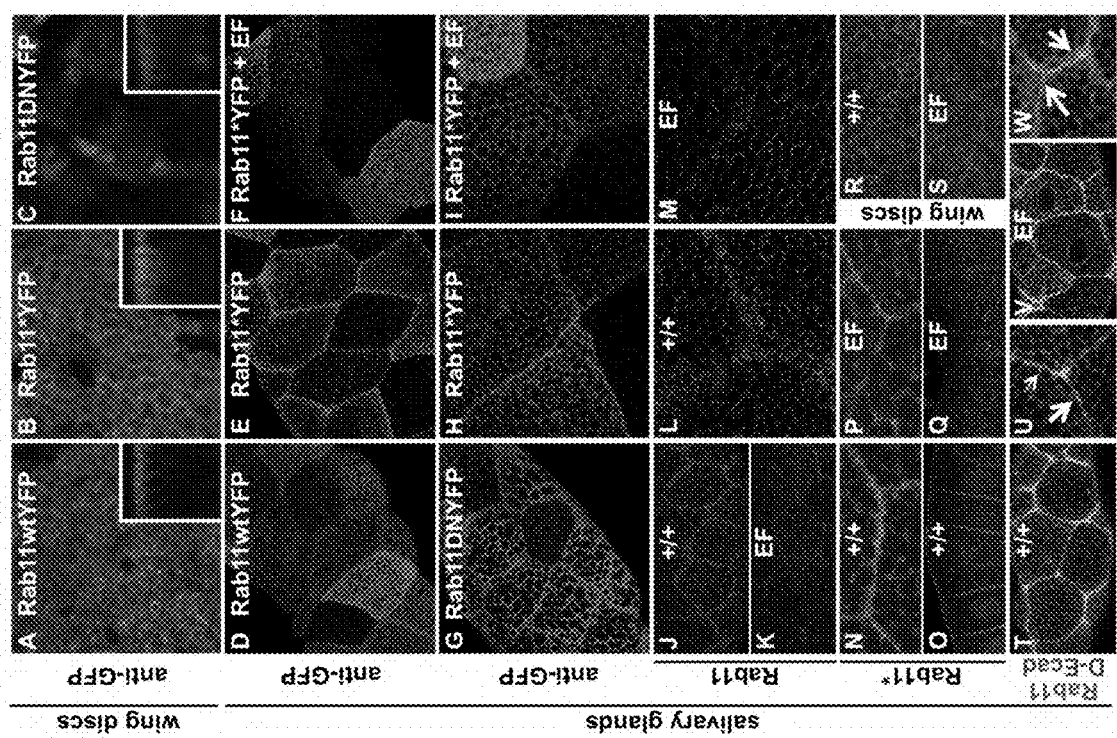
FIGS. 1A-1W show that EF inhibits Rab11 downstream of GTP loading.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

Definitions

To facilitate understanding of the invention, a number of terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The present invention provides, in embodiments, a method for treating a disease in a mammalian subject characterized by compromised epithelial or endothelial barrier integrity or both, comprising administering to a mammalian subject in need thereof an effective amount of a composition comprising an Epac/Rap1 signaling inhibitor. In embodiments, the subject is a human. In embodiments, the disease is anthrax, cholera, or pertussis. In embodiments, the disease is an inflammatory disease. In embodiments, the inflammatory disease is asthma, airway epithelial barrier disruption associated with asthma, atopic dermatitis, eczema, leaky gut syndrome, or inflammatory bowel disease.

The present invention provides, in embodiments, a method for treating a disease in a mammalian subject, wherein the Epac/Rap1 signaling inhibitor is a small molecule inhibitor. In embodiments, the Epac/Rap1 signaling inhibitor is an inhibitor of Epac, Arf6, IGF-1Receptor, or a combination thereof. In embodiments, the Epac/Rap1 signaling inhibitor is ESI-09, SecinH3, Slit, AG1024, or a combination thereof. The invention includes the use of derivatives and analogs of ESI-09, SecinH3, Slit, AG1024, or a combination thereof.

The present invention provides, in embodiments, a method for treating a disease in a mammalian subject, wherein the Epac/Rap1 signaling inhibitor preserves, restores, or both, epithelial barrier integrity, endothelial barrier integrity, or both. The present invention provides, in embodiments, a method for treating a disease in a mammalian subject, wherein the Epac/Rap1 signaling inhibitor is administered as part of an oral rehydration formula or an IV fluid.

The present invention provides, in embodiments, a pharmaceutical composition for treating a disease characterized by compromised epithelial or endothelial barrier integrity comprising: a Epac/Rap1 signaling inhibitor; and a pharmaceutically acceptable carrier.

The present invention provides, in embodiments, a pharmaceutical composition for treating a disease, wherein the pharmaceutical composition protects against the barrier disruptive effects of Anthrax Edema Toxin and Cholera Toxin. The present invention provides, in embodiments, a pharmaceutical composition for treating a disease, wherein the disease is anthrax, cholera, or pertussis. The present invention provides, in embodiments, a pharmaceutical composition for treating a disease, wherein the disease is an inflammatory disease. The present invention provides, in embodiments, a pharmaceutical composition for treating a disease, wherein the inflammatory disease is asthma, airway epithelial barrier disruption associated with asthma, atopic dermatitis, eczema, leaky gut syndrome, or inflammatory bowel disease. The present invention provides, in embodiments, a pharmaceutical composition for treating a disease, wherein the Epac/Rap1 signaling inhibitor is a small molecule inhibitor.

The present invention provides, in embodiments, a pharmaceutical composition for treating a disease, wherein the Epac/Rap1 signaling inhibitor is an inhibitor of Epac, Arf6, IGF-1Receptor, or a combination thereof. The present invention provides, in embodiments, a pharmaceutical composition for treating a disease, wherein the Epac/Rap1 signaling inhibitor is ESI-09, SecinH3, Slit, AG1024, derivatives, analogs thereof, or a combination thereof.

The present invention provides, in embodiments, a pharmaceutical composition for treating a disease, wherein the Epac/Rap1 signaling inhibitor preserves, restores, or both, epithelial barrier integrity, endothelial barrier integrity, or both. The present invention provides, in embodiments, a pharmaceutical composition for treating a disease, wherein the composition is formulated for oral or IV delivery.

As used herein, a "subject in need" refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a primate, including a monkey and a chimpanzee.

The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug. As used herein, pharmaceutically active agents include synthetic or naturally occurring small molecule drugs and more complex biological molecules.

The term "antibody" as used herein encompasses monoclonal antibodies (including full length monoclonal antibodies), polyclonal antibodies, multi-specific antibodies (e.g., bi-specific antibodies), and antibody fragments so long as they exhibit the desired biological activity of binding to a target antigenic site and its isoforms of interest. The term "antibody fragments" comprise a portion of a full length antibody, generally the antigen binding or variable region thereof. The term "antibody" as used herein encompasses any antibodies derived from any species and resources, including but not limited to, human antibody, rat antibody, mouse antibody, rabbit antibody, and so on, and can be synthetically made or naturally-occurring.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The invention may also refer to any oligonucleotides (antisense oligonucleotide agents), polynucleotides (e.g. therapeutic DNA), ribozymes, DNA aptamers, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of compounds, such as a Epac/Rap1 signaling inhibitor, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

Pharmaceutically acceptable carrier: The terms "pharmaceutically acceptable carrier" as used herein refers to an excipient, diluent, preservative, solubilizer, emulsifier, adjuvant, and/or vehicle with which a compound, such as a Epac/Rap1 signaling inhibitor, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminenetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the sections below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

The pharmaceutical compositions comprising a Epac/Rap1 signaling inhibitor, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of a Epac/Rap1 signaling inhibitor, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and a Epac/Rap1 signaling inhibitor, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. A Epac/Rap1 signaling inhibitor, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, a Epac/Rap1 signaling inhibitor, alone or in combination with another active ingredient, may be provided in a solid form, such as a tablet or capsule, or as a solution, emulsion, or suspension. To prepare the oral compositions, a Epac/Rap1 signaling inhibitor, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, a Epac/Rap1 signaling inhibitor, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, a Epac/Rap1 signaling inhibitor, alone or in combination with other active ingredient(s), may be administered using, for example, a spray formulation also containing a suitable carrier.

For topical applications, a Epac/Rap1 signaling inhibitor, alone or in combination with other active ingredient(s), are preferably formulated as creams or ointments or a similar vehicle suitable for topical administration. For topical administration, a Epac/Rap1 signaling inhibitor, alone or in combination with other active ingredient(s), may be mixed with a pharmaceutical carrier at a concentration of about 0.1% to about 10% of drug to vehicle. Another mode of administering a Epac/Rap1 signaling inhibitor, alone or in combination with other active ingredient(s), may utilize a patch formulation to effect transdermal delivery.

One of ordinary skill in the art may modify the formulations within the teachings of the specification to provide numerous formulations for a particular route of administration. In particular, a Epac/Rap1 signaling inhibitor, alone or in combination with other active ingredient(s), may be modified to render them more soluble in water or other vehicle. It is also well within the ordinary skill of the art to modify the route of administration and dosage regimen of a particular Epac/Rap1 signaling inhibitor, alone or in combination with other active ingredient(s), in order to manage the pharmacokinetics of the present compounds for maximum beneficial effect in a patient.

A more complete understanding can be obtained by reference to the following specific examples which are provided herein for purposes of illustration only, and are not intended to limit the scope of the invention.

Examples

The invention provides a therapeutic approach for the molecular pathways connecting ET or Ctx induced cAMP overload to inhibition of Rab11. A combination of approaches was employed involving GTPase isoform-specific transgenes and antibodies, *Drosophila* epithelial tissues, human cell lines, and in vivo studies in mice. The results indicate that these two cAMP-producing toxins disrupt Rab11-dependent processes following the GTP loading step. In flies, both cAMP effectors PKA and Epac participate in the disruption of Rab11-mediated junctional transport, but act at early versus late steps of the trafficking process, respectively. In mammalian systems, the Epac/Rap1 pathway serves as the primary mediator of EF-induced toxemia. Arf6, a small GTPase involved in endocytic retrieval of junctional proteins [25], causes phenotypes nearly identical to those of EF and Ctx when activated, and similarly alters Rab11 levels and distribution. Chemical inhibition of Epac (using ESI-09) or Arf6 (using SecinH3 [26] or Slit [27]), can fully reverse the effect of EF in a mouse footpad edema assay or in human cells. These latter findings indicate new therapeutic avenues for alleviating pathological effects of cAMP toxins and other barrier disruptive agents.

In some aspects, a multi-system analysis of the mechanism by which EF inhibits Rab11 and exocyst-dependent trafficking is presented. Epistasis experiments in *Drosophila* reveal that over-activation of the cAMP effectors PKA and Epac/Rap1 interferes with Rab11-mediated trafficking at two distinct steps. The invention describes conserved roles of Epac and the small GTPase Arf6 in ET-mediated disruption of vesicular trafficking and showed that chemical inhibition of either pathway greatly alleviates ET-induced edema. Thus, the invention defines Epac and Arf6 as drug targets for the treatment of infectious diseases and other pathologies involving cAMP overload or barrier disruption.

In some aspects, the invention provides a further mechanistic dissection of Rab11 inhibition by cAMP-inducing toxins using a combination of *Drosophila* and mammalian systems. EF and Ctx block Rab11 trafficking after the GTP-loading step, as they prevent a constitutively active form of Rab11 from delivering cargo vesicles at the plasma membrane. Both primary cAMP effectors, PKA and Epac, contribute to this effect, however these two pathways act at distinct steps of the delivery process. PKA acts early, preventing Rab11 from associating with its effectors Rip11 and Sec15, while Epac functions subsequently via the small GTPase Rap1 to block fusion of recycling endosomes with the plasma membrane. In mammalian systems, Epac/Rap1 appears to be the primary effector branch mediating the effects of EF both in cell culture and in vivo. The small GTPase Arf6, which initiates endocytic retrieval of adhesion components, also contributes to junctional homeostasis by counteracting Rab11-dependent delivery of cargo proteins at sites of cell-cell contact. Notably, chemical inhibition of either Arf6 or Epac blocks the effect of EF in cell culture and in vivo, indicating a new therapeutic avenue for treating symptoms caused by cAMP-inducing toxins or other barrier-disrupting pathologies.

Figures 15A, 15O:
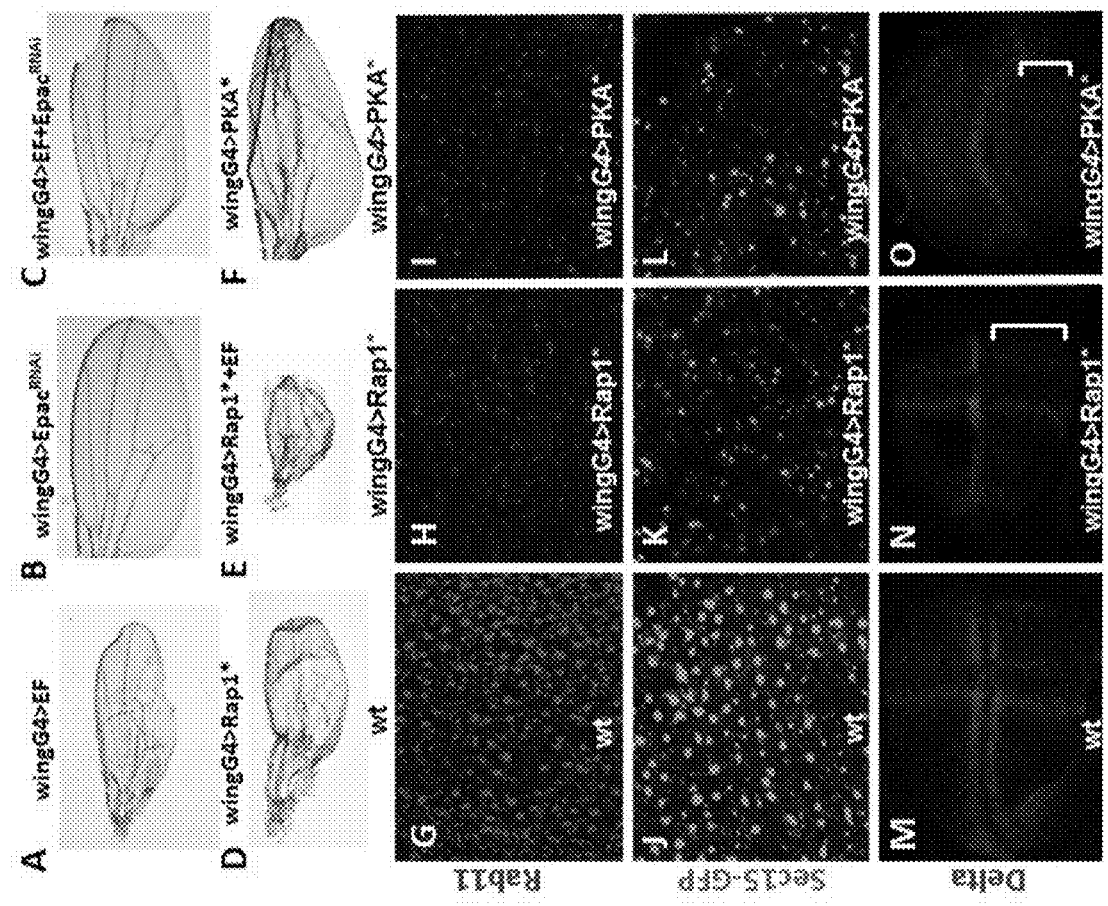
FIGS. 15A-15O shows genetic evidence that phenotypes caused by EF in Drosophila depends on the Epac/Rap1 pathway.

In some aspects, ESI-09 is a small molecule that competitively binds to the cAMP binding site on Epac and prevents activation of Epac as a guanine nucleotide exchange factor specific for Rap1. Therefore, ESI-09 prevents conversion of inactive GDP bound Rap1 to the active GTP bound form induced by camp via activation of Epac. Experiments with ESI-09 in human cell culture or in vivo in mice (FIGS. 16A-16E) corroborate genetic experiments performed in the fruit fly (*Drosophila melanogaster*) (FIGS. 15A-15O), that all point to inhibition of Epac/Rap1 as an effective means for reducing the barrier disrupting effects of cAMP toxins such as ET and CT. Strong, although less persistent, suppression of footpad swelling was observed with AG1024, which may act by inhibiting Rap1 (i.e., via blocking IGF-1R stimulation of Rap1).

Results cAMP-Inducing Toxins Block Rab11 Activity Following GTP Loading but Prior to Exocyst Assembly To better understand how cAMP-inducing toxins block Rab11-dependent trafficking, the behaviors of three forms of Rab11: wild-type (wt), activated (*), and Dominant-Negative (DN) [28] were initially examined. These variants were first expressed in the wing primordium where the inhibition of Rab11 by EF and Ctx was initially discovered and analyzed [20,23]. The sub-cellular distribution of Rab11wt detected by immuno-fluorescence appeared as a grainy stain restricted primarily to the apical pole of epithelial cells (FIG. 1A). In addition to this wild-type pattern, activated Rab11 (Rab11*), a constitutively active form that cannot hydrolyze GTP to GDP, displayed an additional staining component that accumulates at or near adherens apical junctions (AJs) (FIG. 1B). This latter staining is in line with the known role of Rab11 in junctional delivery (see FIGS. 7A-7F for co-localization of Rab11* and *Drosophila* E-cadherin (D-Ecad)). It was concluded that active GTP-bound Rab11 is selectively directed to cell-cell contacts at AJs. Consistent with this finding, dominant-negative Rab11 (Rab11DN), which remains in the inactive GDP-bound form, did not localize to junctions or accumulate apically (FIG. 1C). Next the analysis was turned to larval salivary glands, which are comprised of large polyploid secretory cells[29], and in which the junctional specific distribution of Rab11* is more pronounced than in larval salivary glands. In these cells, over-expressed Rab11wt was present throughout the cytoplasm, albeit excluded from densely packed secretory granules, with higher levels detected in the vicinity of intercellular junctions (FIG. 1D). Rab11* behaved similarly but, in addition, exhibited a strong junctional staining component (FIGS. 1E and 1H). In contrast, Rab11DN did not display any preferential distribution at junctions. However, Rab11DN altered the size and shape of secretory granules (FIG. 1G), suggesting that Rab11 normally plays a role in the formation or trafficking of these granules. These findings in the salivary gland confirm results in wing discs suggesting that the activated GTP-bound form of Rab11 is selectively directed to AJs.

Figures 8A, 8B, 8C:
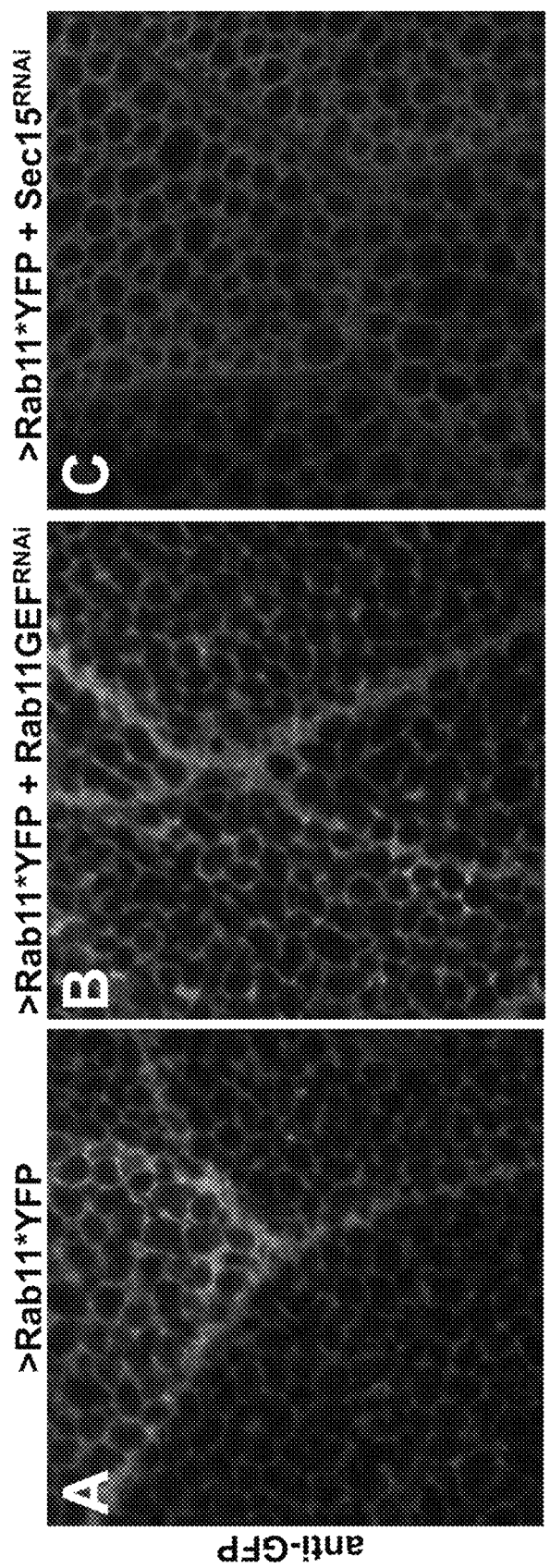
FIGS. 8A-8C show that blocking expression of Sec15, but not of the Rab11GEF Crag, prevents Rab11*-YFP targeting to cell junctions in Drosophila salivary glands. Blocking expression of Sec15, but not of the Rab11GEF Crag, prevents Rab11*-YFP targeting to cell junctions in Drosophila salivary glands.
Figures 9A, 9B:
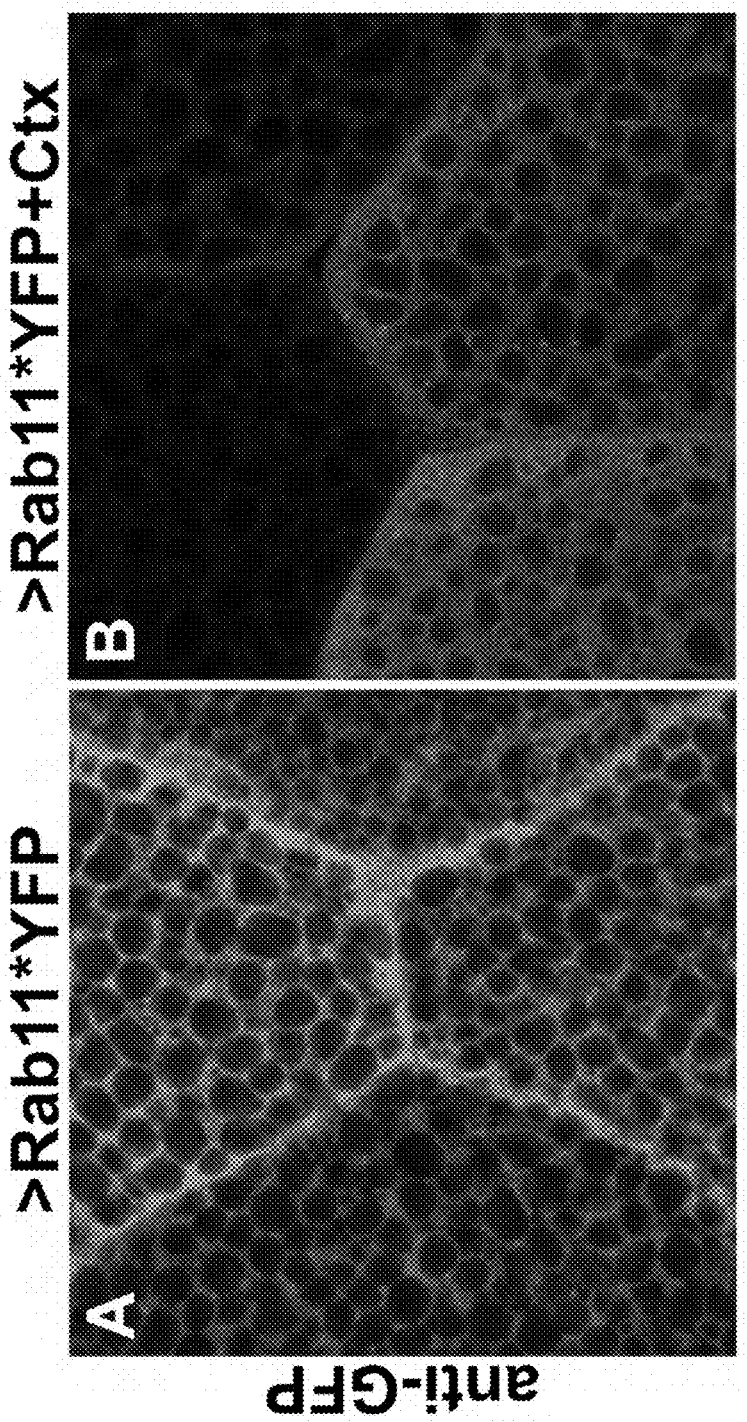
FIGS. 9A-9B show that Ctx prevents Rab11*-YFP targeting to cell junctions.

According to the present model, factors regulating Rab11 upstream of the GTP-loading step should have no effect on Rab11* distribution, while inhibitory factors acting downstream of Rab11 should prevent Rab11* from accumulating at AJs. To test this model, an RNAi construct that blocks expression of Sec15, an important Rab11 effector required for junctional delivery [16], was employed. Sec15-RNAi clearly prevented Rab11* from reaching the AJs (FIG. 8), consistent with Sec15 acting downstream of Rab11, following the activation step. In contrast, an RNAi construct blocking expression of Crag, the single known Rab11 GEF [30], had no affect on Rab11* distribution, consistent with Crag acting upstream of Rab11 (FIGS. 8A-8C). In order to determine whether EF and Ctx block activation (GTP loading) of Rab11 or a subsequent step, these toxins were co-expressed with Rab11* and its localization was examined. It was found that expression of either toxin prevented Rab11* junctional accumulation (FIG. 1F, compare FIGS. 1H and 1I for higher magnifications, and FIGS. 9A-9B). As the artificially activated Rab11* remains sensitive to EF and Ctx action, it was concluded that these toxins act after the GTP loading step.

The behavior of endogenous Rab11 in salivary glands and its response to EF challenge was examined next. In wild-type glands, Rab11 shows a granular distribution with a higher concentration in the vicinity of cell junctions (FIGS. 1J and 1L), which may represent an enrichment in the activated fraction of Rab11. In EF-expressing glands, this juxta-junctional staining was clearly reduced. Rab11 dots were detected at similar levels as in wild-type glands, but very few accumulated around the junctions (FIGS. 1K and 1M). These findings are consistent with the model that EF prevents activated Rab11 from reaching the AJs. To test this model further, an antibody that specifically detects the activated Rab11* pool was employed. Consistent with the observations described above, it was found that the endogenous activated Rab11 localizes predominantly to AJs (FIGS. 1N and 1O). In EF-expressing glands, total levels of Rab11* are not obviously altered, however, less Rab11* accumulated at the AJs (FIGS. 1P and 1Q). Similarly, in EF-expressing discs, activated Rab11 levels remained comparable to wild-type levels while junctional accumulation was severely reduced by EF (FIGS. 1R and 1S). It was concluded that EF and Ctx do not interfere with Rab11 activation (GTP loading), but instead block Rab11 function at a subsequent step(s) to prevent activated Rab11 from trafficking to AJs.

Figures 10A, 10B, 10C, 10D, 10E, 10F, 10G, 10H, 10I, 10J, 10K, 10L:
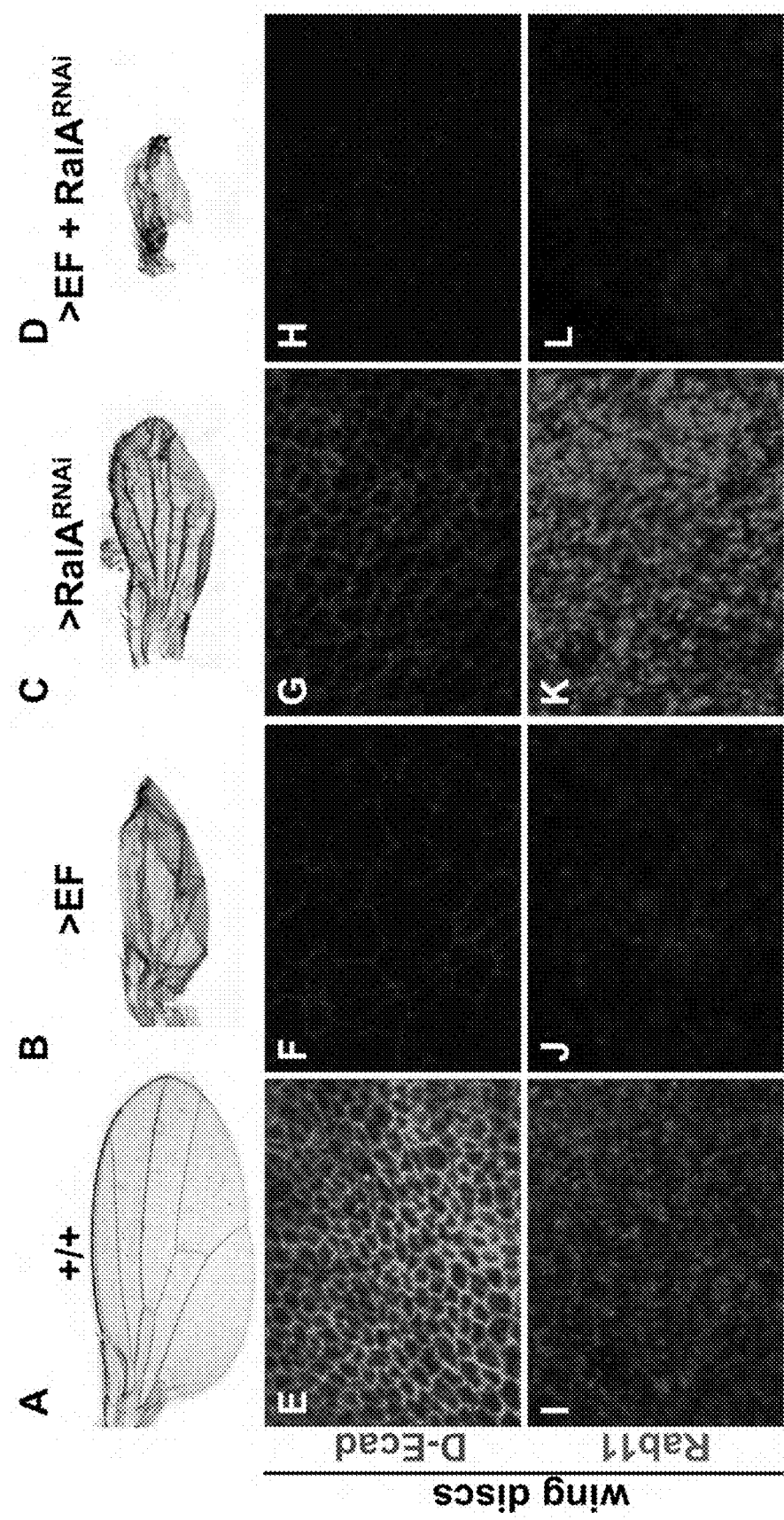
FIGS. 10A-10L show similar effects of EF and RalARNAi on wing phenotypes but their divergent effects on Rab11 levels reveal that EF acts upstream of RalA. Similar effects of EF and RalARNAi on wing phenotypes but their divergent effects on Rab11 levels reveal that EF acts upstream of RalA.

Next, it was tested whether the association between Rab11 and its known cargo protein D-Ecad was affected by EF. As expected, co-labeling of Rab11 and D-Ecad in wild-type salivary glands revealed strong co-localization at cell junctions (FIGS. 1T and 1U—wide arrow—) or in punctate structures near the junctions (FIG. 1U—thin arrow—). In glands expressing EF, D-Ecad was still concentrated near AJs, suggesting that Rab11-dependent trafficking may not be the only route for cadherins to traffic to the proximity of the plasma membrane in this tissue. However, Rab11-DEcad co-localization was abrogated (FIGS. 1V and 1W, wide arrows). In addition, some areas showed a gap between cells (FIG. 1W, upper arrow), suggesting that D-Ecad may approach junctions but then fail to insert in the plasma membrane via vesicular fusion as a consequence of EF activity, leading to weakened AJs. It was concluded that EF blocks the association between Rab11 and recycling vesicles containing cargo proteins such as D-Ecad.

cAMP can lead indirectly to stimulation of RalA [31], a small GTPase which associates with core exocyst components and involved in exocyst assembly [32]. The effect of inhibiting RalA by knocking down RalA expression using RNAi was therefore tested and a wing phenotype similar to that caused by EF was observed (FIGS. 10A-10B). Furthermore, RNAi of RalA in combination with EF resulted in a strong synergistic phenotype typical of inhibition of Rab11 (FIG. 10C). As expected, this effect was reflected in reduced levels of apical D-Ecad in the developing wing in wings expressing EF, RalA, or both (FIGS. 10E-10H). Surprisingly, however, RalA-RNAi altered Rab11 levels in a manner opposite to that of EF. Namely, instead of reducing Rab11 staining (as caused by EF or Ctx), RalA-RNAi, substantially increased Rab11 levels (FIG. 10K). These elevated levels of Rab11 may reflect a homeostatic feedback process responding to inhibition of Rab11 function, or might result from an accumulation at the point of blockage in Rab11 trafficking. When EF was co-expressed with RalA-RNAi, the EF phenotype prevailed, as manifest by low Rab11 levels similar to those observed with EF alone (FIG. 10L). This latter finding is consistent with EF acting indirectly upstream of RalA in its role in exocyst-mediated vesicle docking at the plasma membrane, rather than RalA being a direct cAMP-dependent effector of EF as discussed further below.

Figures 2A, 2B, 2C, 2D, 2E, 2F, 2G, 2H, 2I, 2J, 2K, 2L, 2M:
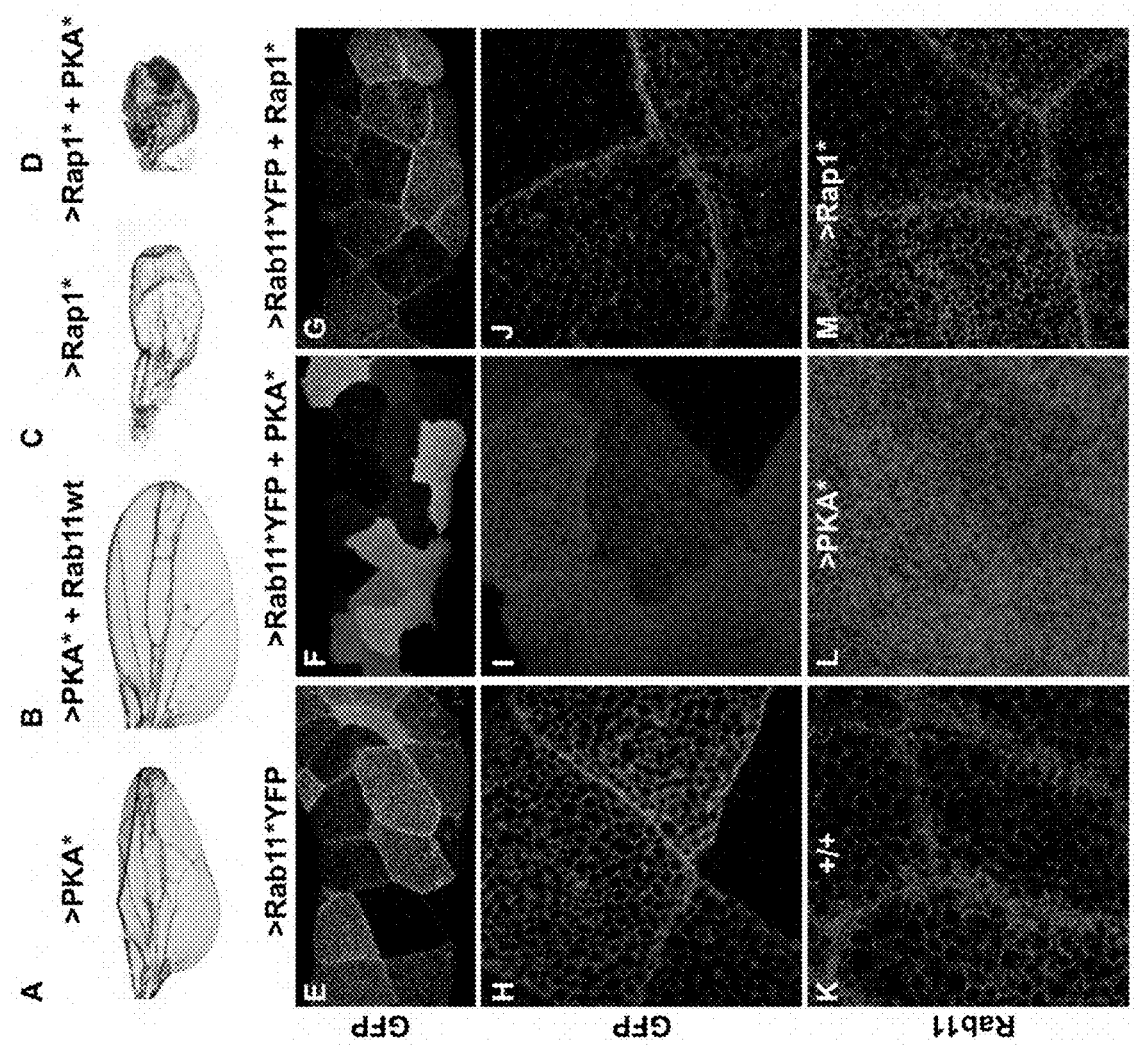
FIGS. 2A-2M show that PKA* and Rap1* block Rab11 at distinct steps of junctional trafficking.

PKA and Epac Block Rab11 Trafficking at Distinct Steps cAMP stimulates two main effectors: PKA and Epac, a GEF activating the small GTPase Rap1 [33] [34]. In order to mimic activation of each branch of the cAMP pathway separately, a constitutively active form of PKA (PKA*, consisting of the catalytic domain only [35]) and an activated form of Rap1 (Rap1*, which is unable to hydrolyze GTP to GDP [31]) were made use of. Expression of either construct in the wing primordium caused a phenotype similar to that of EF or Ctx, consisting of blistered wings with thickened veins (FIGS. 2A and 2C). Consistent with these phenotypes being mediated, at least in part, by inhibition of Rab11, it was previously reported that both PKA* and Rap1* caused a reduction in Rab11 levels, blocked accumulation of apical Delta, and prevented the formation of Sec15 structures in the wing primordium [23]. Following up on these observations, it was found that co-expression of Rap1* and PKA* caused a much stronger synergistic phenotype, suggesting that these effectors disrupt a common pathway (FIG. 2D). Furthermore, the PKA* phenotype was partially rescued by co-expression with Rab11wt (FIG. 2B), lending further support to the idea that excessive PKA activation inhibits Rab11. To compare the respective activities of PKA and Rap1 on Rab11 function, the activated form of Rab11 was co-expressed with either PKA* or Rap1*. PKA* profoundly altered the distribution of Rab11*, both by completely blocking accumulation of Rab11* at AJs (FIGS. 2F and 2I, compare with FIGS. 2E and 2H) in a similar, albeit stronger, fashion as EF or Ctx, and also by preventing the formation of secretory granules (or dramatically reducing their size). These combined effects result in Rab11* being ubiquitously distributed throughout the cytoplasm (FIGS. 2F and 2I). A similar pattern was observed when staining for total endogenous Rab11, which lost its tendency to be concentrated near junctions in response to PKA* expression (FIG. 2L, compare with FIG. 2K). Interestingly, PKA* induced a strong increase in Rab11 levels in salivary glands, which is opposite to its effect in wing imaginal discs [20,23]. In contrast to the effects of PKA*, expression of Rap1* in salivary glands did not prevent Rab11* from accumulating near cell boundaries (FIGS. 2G and 2J). However, instead of the typical single sharp line coinciding with cell junctions observed with Rab11* alone, co-expression with Rap1* resulted in a double row of Rab11* staining, revealing a narrow gap between adjacent cells (FIG. 2J). This phenotype suggests a failure of the final fusion event between cargo vesicles and the plasma membrane. Consistent with these observations, endogenous total Rab11 staining was also more conspicuously concentrated in the vicinity of cell boundaries in response to Rap1* expression (FIG. 2M).

EF and PKA* Prevent Association of Rab11* with its Effectors Rip11 and Sec15

Figures 3A, 3B, 3C, 3D, 3E, 3F, 3G, 3H, 3I, 3J, 3K:
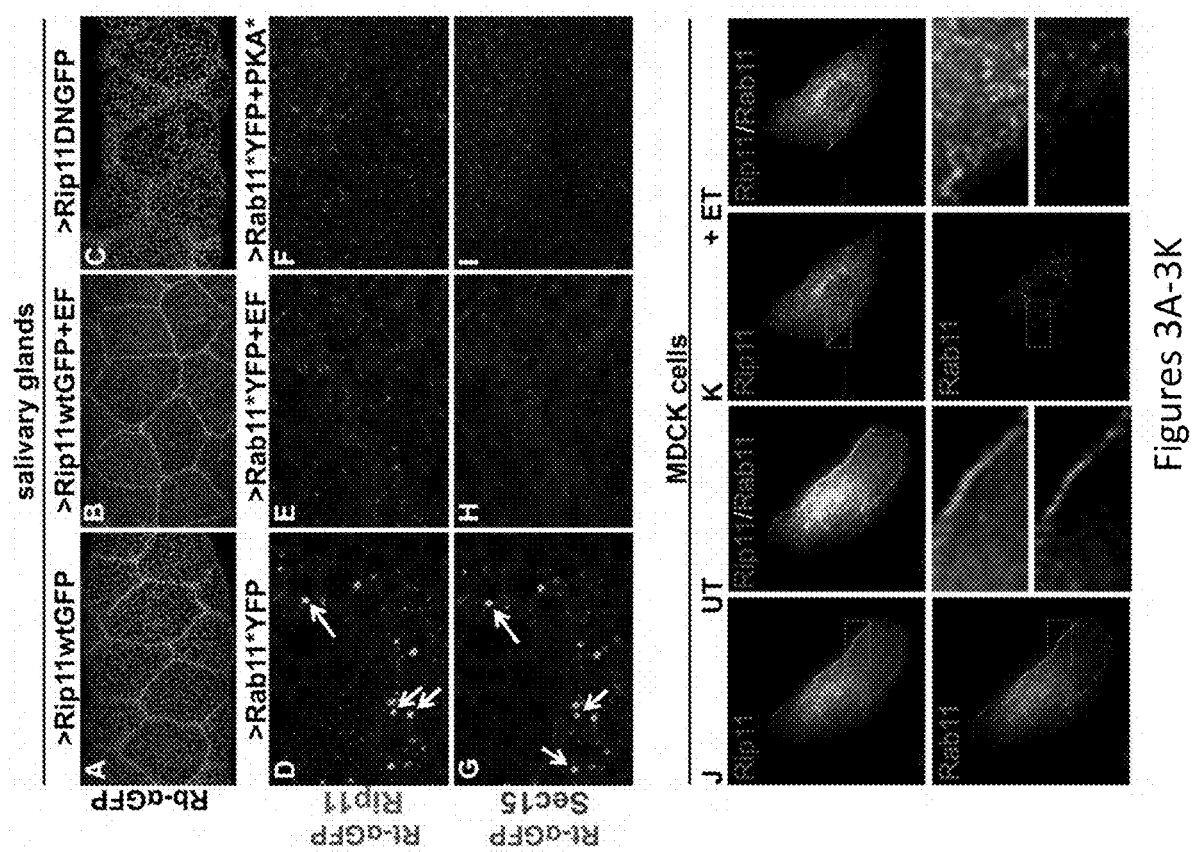
FIGS. 3A-3K show that EF and PKA* prevent association between Rab11* and its effectors Rip11 and Sec15.

In order to direct cargo vesicles to the AJs and promote their fusion with the plasma membrane Rab11 must interact with several known effectors including Rab11-FIPs (Rab11 Family-Interacting Proteins [36]) and Sec15, a component of the exocyst complex that is critical for its assembly [17]. Drosophila has single orthologs of Rab11-FIP (dRip11 [37]), as well as unique representatives of all core exocyst components, [16]. To test the effect of EF on Rab11 effectors, a full length GFP-tagged dRip11 UAS-transgene [37] in the salivary glands was first expressed and it was observed that this fusion protein was strongly concentrated at cell junctions (FIG. 3A). Co-expression of EF with dRip11 reduced, but did not eliminate junctional accumulation of dRip11 and also resulted in forked and irregular cell borders (FIG. 3B). Since Rip11 is a Rab11 binding protein, the association between these two proteins was also examined, which was visualized by expressing Rab11* (detected with a rat anti-GFP antibody) and staining for the endogenous dRip11. This particular double stain revealed frequent co-localization of the two proteins in bright dots in the vicinity of intercellular junctions (FIG. 3D, arrows). It was found that co-expression of EF or PKA* with Rab11* completely abolished its co-localization with Rip11 (FIGS. 3E and 3F), strongly supporting the idea that high levels of cAMP trigger a dissociation of Rab11 and Rip11. Similarly, a stain for Sec15 revealed an identical loss of Rab11*/Sec15 co-localization upon EF or PKA* expression (FIGS. 3G-3I). In contrast, Rap1* did not disrupt co-localization of either Rab11*/Rip11 or Rab11*/Sec15.

Figures 11A, 11B, 11C, 11D, 11E, 11F:
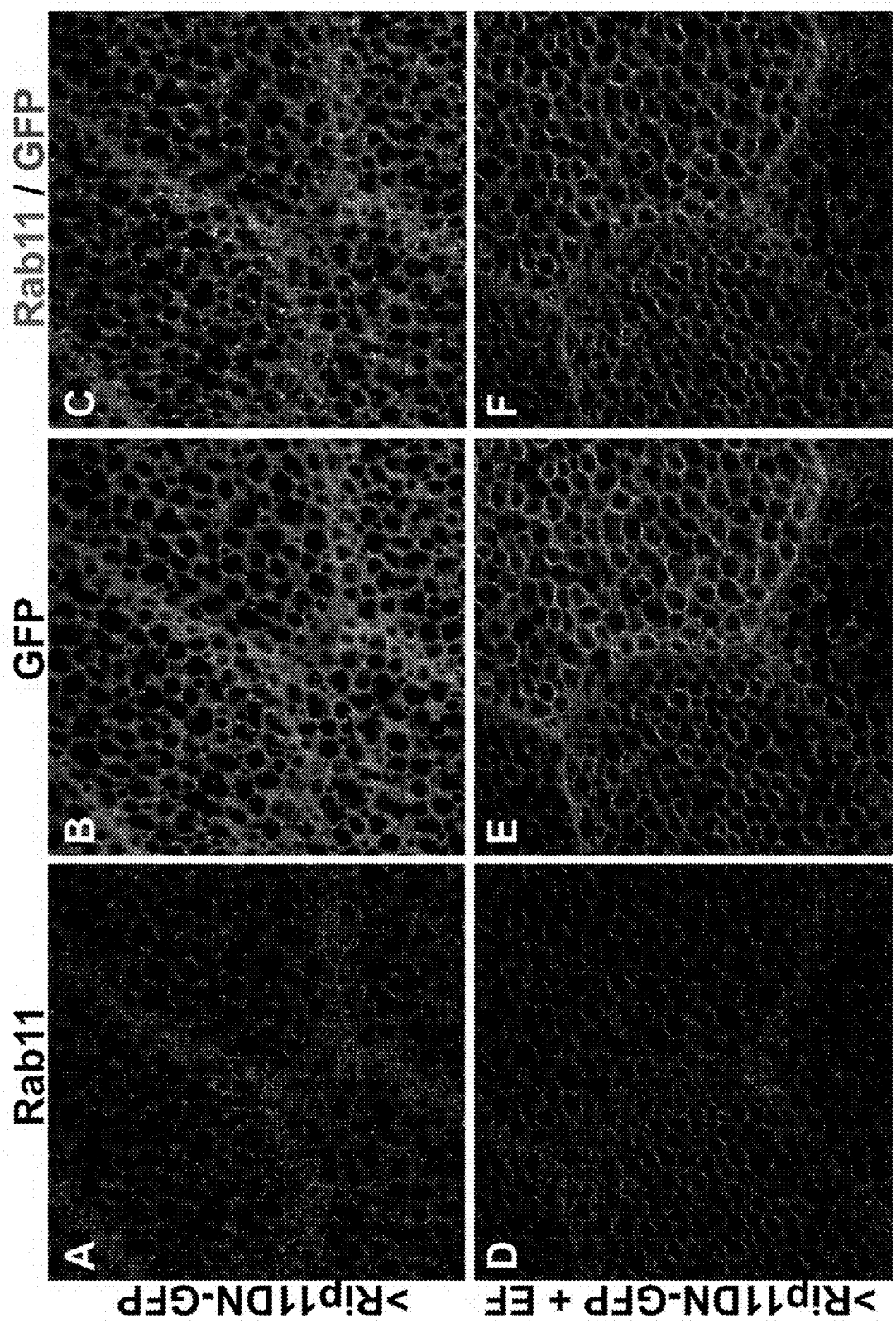
FIGS. 11A-11F show that EF does not disrupt dRip11DN/Rab11 co-localization in salivary glands.

Because mammalian Rip11 is a substrate of PKA [38], it was wondered whether phosphorylation of Rip11 might play a role in mediating the inhibition of Rab11 by cAMP toxins. In contrast to full-length Rip11, a truncated dominant-negative form of d-Rip11 (d-Rip11DN) retaining only the C-terminal Rab11-binding domain[37], did not accumulate at junctions, consistent with its N-terminal cholesterol-binding domain being essential for the Rip11-Rab11 complex and cargo vesicles to traffic to AJs. Instead, d-Rip11DN was distributed in a granular pattern throughout the cytoplasm, although it did show higher levels near AJs (FIG. 3C, and FIG. 11). Also, small dRip11DN cytoplasmic punctae strongly co-localized with Rab11 (FIGS. 11A-11C), consistent with d-Rip11DN retaining the Rab11-binding domain. Interestingly, when co-expressed with EF, this co-localization was not reduced, but rather transformed into rings that encircled secretory granules (FIGS. 11D-11F). Thus, EF appears to alter the membrane compartment with which the Rab11-Rip11 complex associates but does not abrogate association between the two proteins. In aggregate, these results suggested that cAMP acts via PKA to trigger dissociation of Rab11*/Rip11 complexes. Because deletion of the first 700 aa of Rip11 (a region containing a verified PKA phosphorylation site in humans [38] and several such predicted sites in Drosophila) results in an EF-resistant association between Rab11* and d-Rip11DN, dissociation of the full length Rip11 from Rab11 may be induced by PKA phosphorylation.

Figures 12A, 12B, 12C, 12D, 12E, 12F:
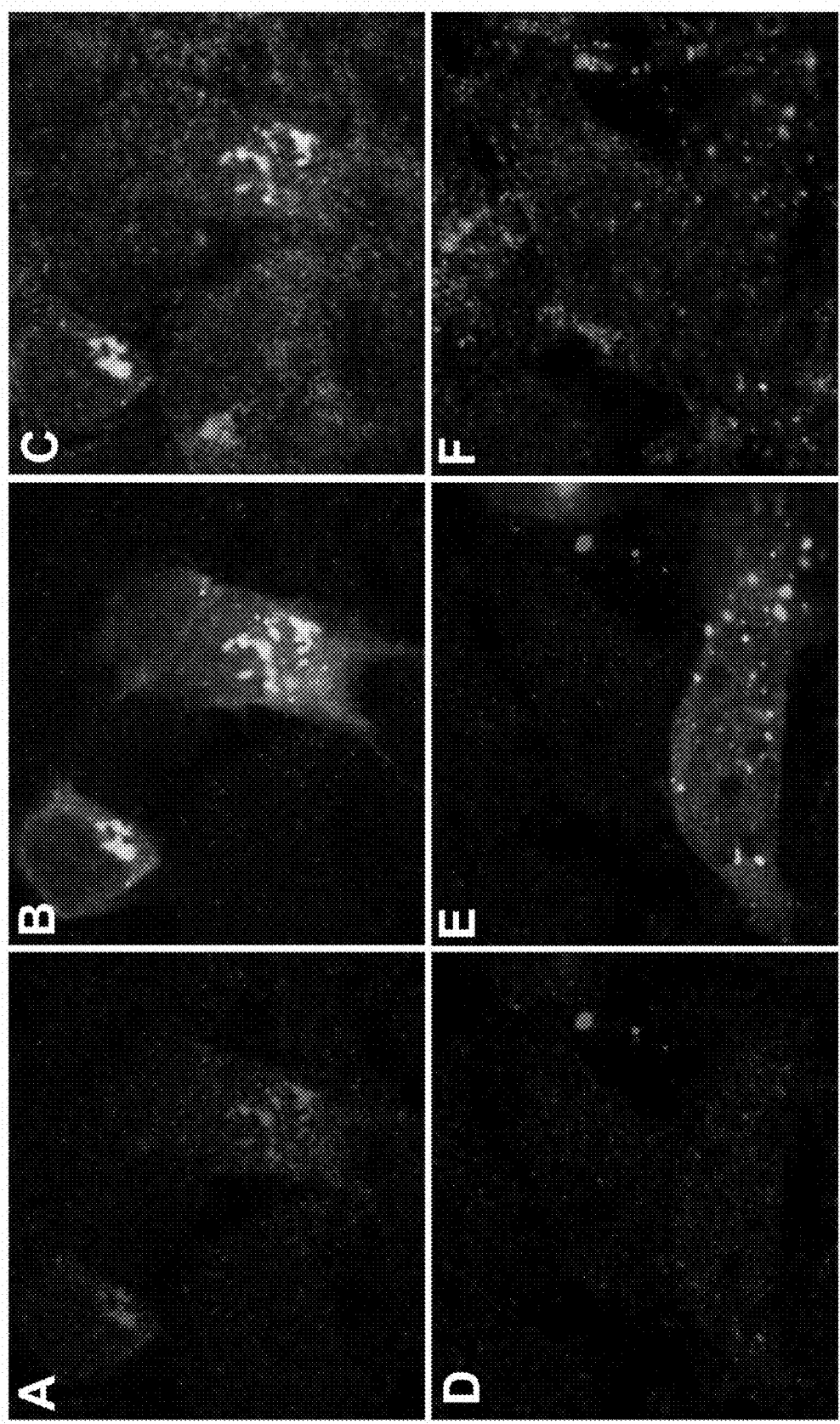
FIGS. 12A-12F show that ET treatment reduces Sec15/Rab11* and Rab11*/Rip11 co-localization in HBMEC cells.

The relationship between Rip11 and Rab11 was next examined in mammalian Madin-Darby Canine Kidney (MDCK) cells, in which the role of Rab11 in Cadherin trafficking is well established [39]. Co-expression of Rab11-DsRed and Rip11-GFP constructs in these cells revealed strong co-localization throughout the cytoplasm, as well as a tendency for the two proteins to accumulate at intercellular junctions (FIG. 3J). When these cells were treated with ET, however, Rab11-Rip11 co-localization was often lost, and Rab11-DsRed failed to reach the plasma membrane. Mirroring the observations in Drosophila salivary glands, Rip11-GFP accumulation at cell boundaries was reduced by ET-treatment (FIG. 3K). Interaction between Rab11* and its effectors can be also tested in Human Brain Microvascular Cells (HBMECs) transfected with a Sec15-GFP construct. High-level expression of Sec15-GFP leads to formation of punctate structures (FIG. 12), the formation of which depends on Rab11 [20]. Consistent with Sec15 associating with the active form of Rab11, a high degree of co-localization was detected between Sec15-GFP fluorescence and the activated form of Rab11 detected by an anti-GTP-Rab11* antibody (FIGS. 12A-12B). In this context of Sec15 over-expression, co-localization of Rab11* with endogenous Rip11 could also be detected (FIGS. 12B-12C). When these cells were treated with ET, Sec15-GFP punctate structures were significantly reduced after 6 hours, and the remaining GFP stain no longer co-localized with Rab11* and Rip11 (FIGS. 12D-12F). Cumulatively, these experiments suggest that EF-induced dissociation of Rab11* and its effectors Rip11 and Sec15 is a well conserved process across species.

Activation of the Small GTPase Arf6 Phenocopies Aspects of EF Treatment

Figures 4A, 4Q:
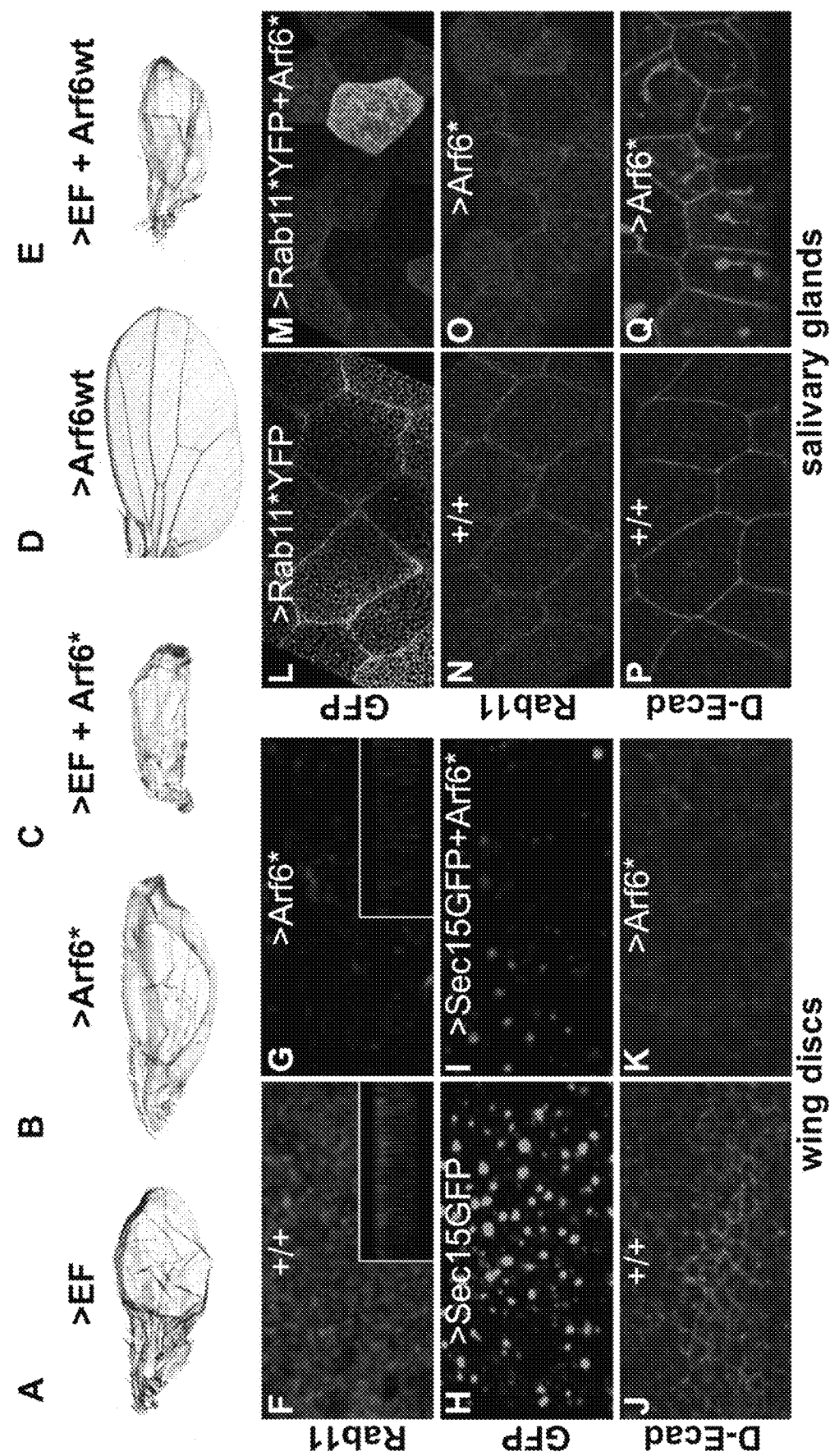
FIGS. 4A-4Q show that activation of Arf6 partially mimics the effect of EF.
Figures 5A, 5B, 5C, 5D, 5E, 5F, 5G, 5H:
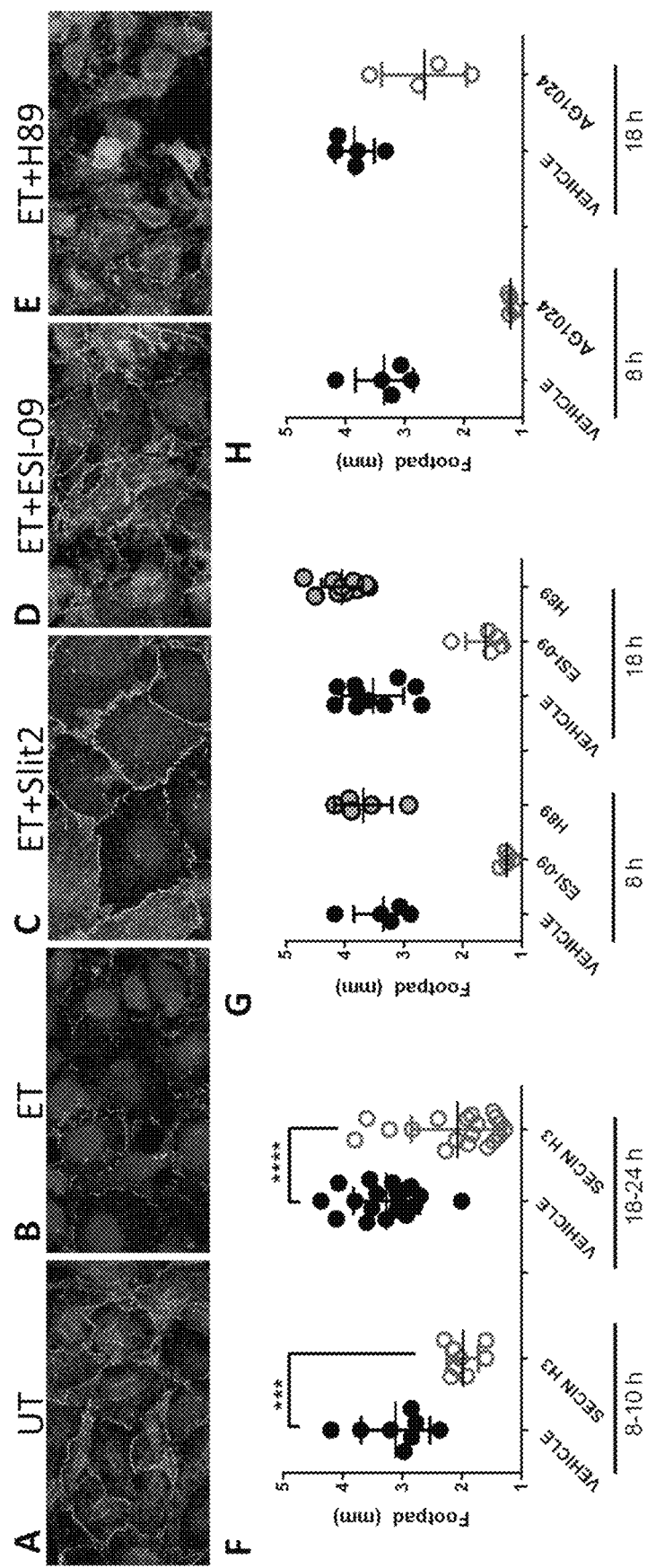
FIGS. 5A-5H show that Arf6 and Rap1 play key roles in mediating EF/Ctx toxicity in mammalian systems.
Figure 6:
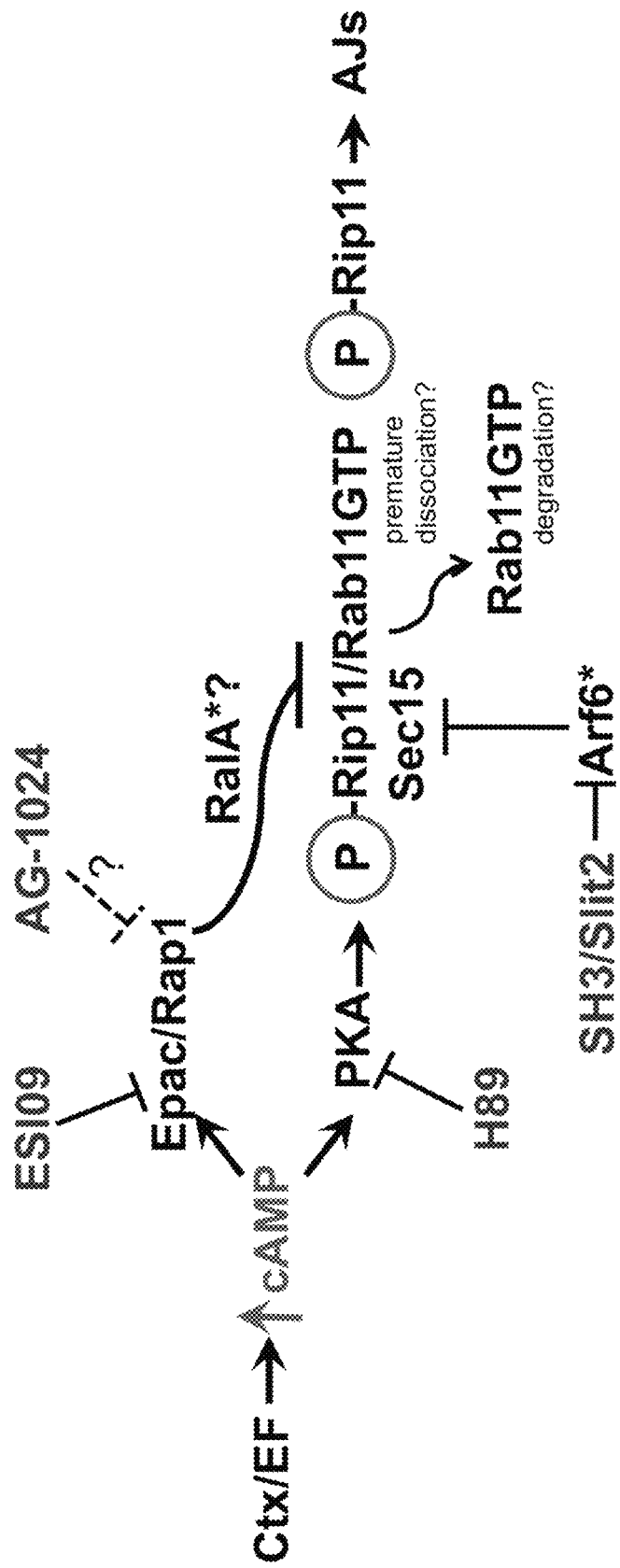
FIG. 6 shows a summary diagram. cAMP overload caused by EF or Ctx can activate either or both of the PKA and Epac/Rap1 effector pathways depending on cellular or organismal context. In this model, uncontrolled PKA stimulation promotes dissociation of Rab11 from its effectors Rip11 and Sec15. Premature dissociation may prevent the activated form of Rab11 (but not Rip11) from reaching the AJs, and thereby block delivery of cargo proteins (e.g., Cadherins and Notch ligands). In some cellular contexts dissociation of Rab11-GTP from Rip11 may also lead to Rab11 degradation (e.g., Drosophila wing discs and human endothelial cells) while in others only to the loss of junctional accumulation (e.g., Drosophila salivary glands and human intestinal epithelial cells). Activation of Rap1 leads to exocyst inhibition, possibly through de-regulation of RalA. The relative contribution of each branch may depend on cell type and organism, although, the Epac/Rap1 branch (blocked by ESI-09, and possibly by AG1024) appears to be the primary mediator of EF in mammalian systems. Arf6 activation also inhibits Rab11* targeting to the AJs, an effect that may be mediated by interaction with exocyst components. Inhibition of Arf6 by SecinH3 or Slit2 provides protection against EF in cultured humans cells and in vivo in mice.
Figures 7A, 7B, 7C, 7D, 7E, 7F:
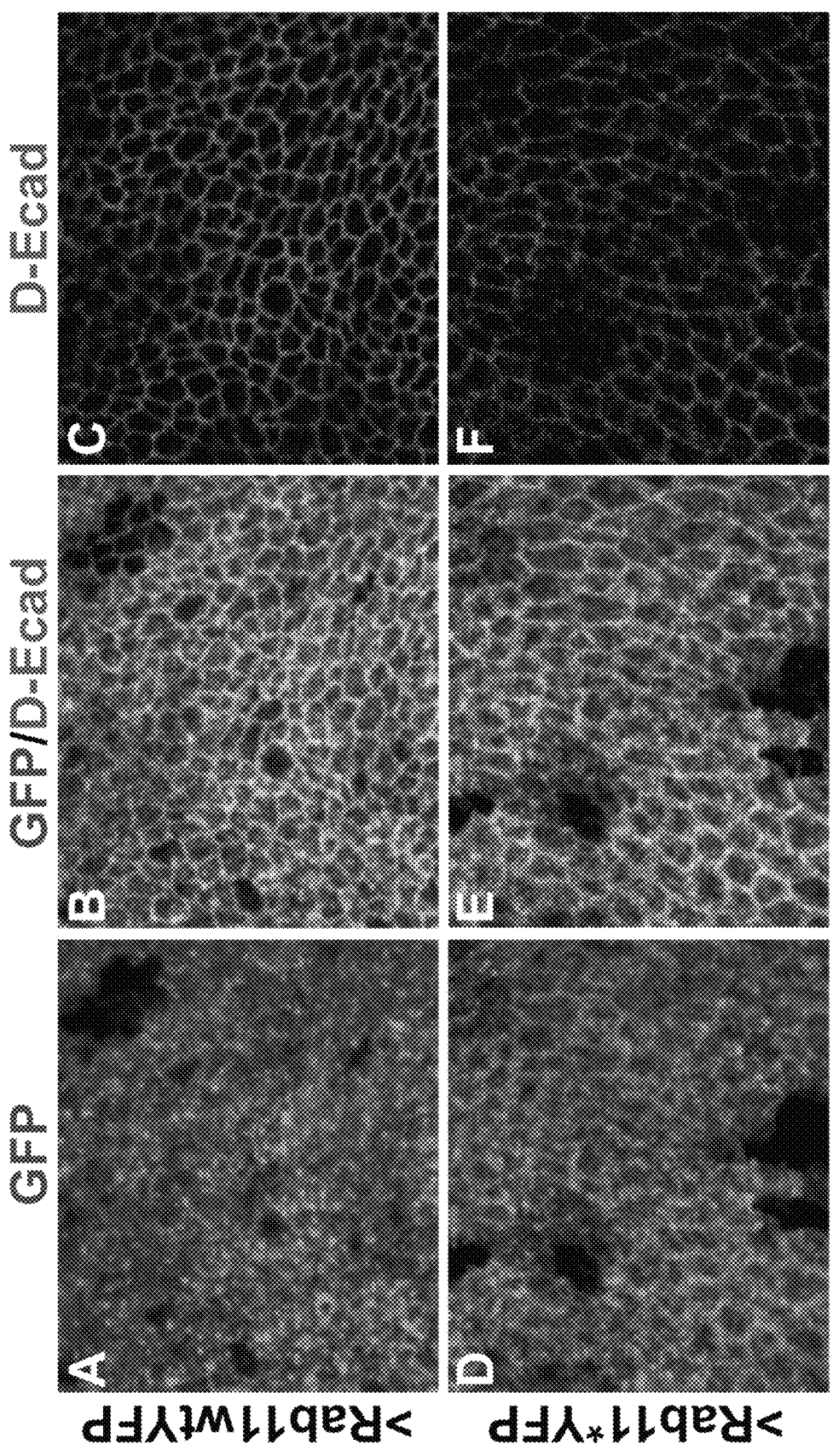
FIGS. 7A-7F show that activated Rab11 (Rab11*) preferentially accumulates at AJs in Drosophila wing imaginal discs.
Figures 13A, 13B, 13C, 13D, 13E, 13F:
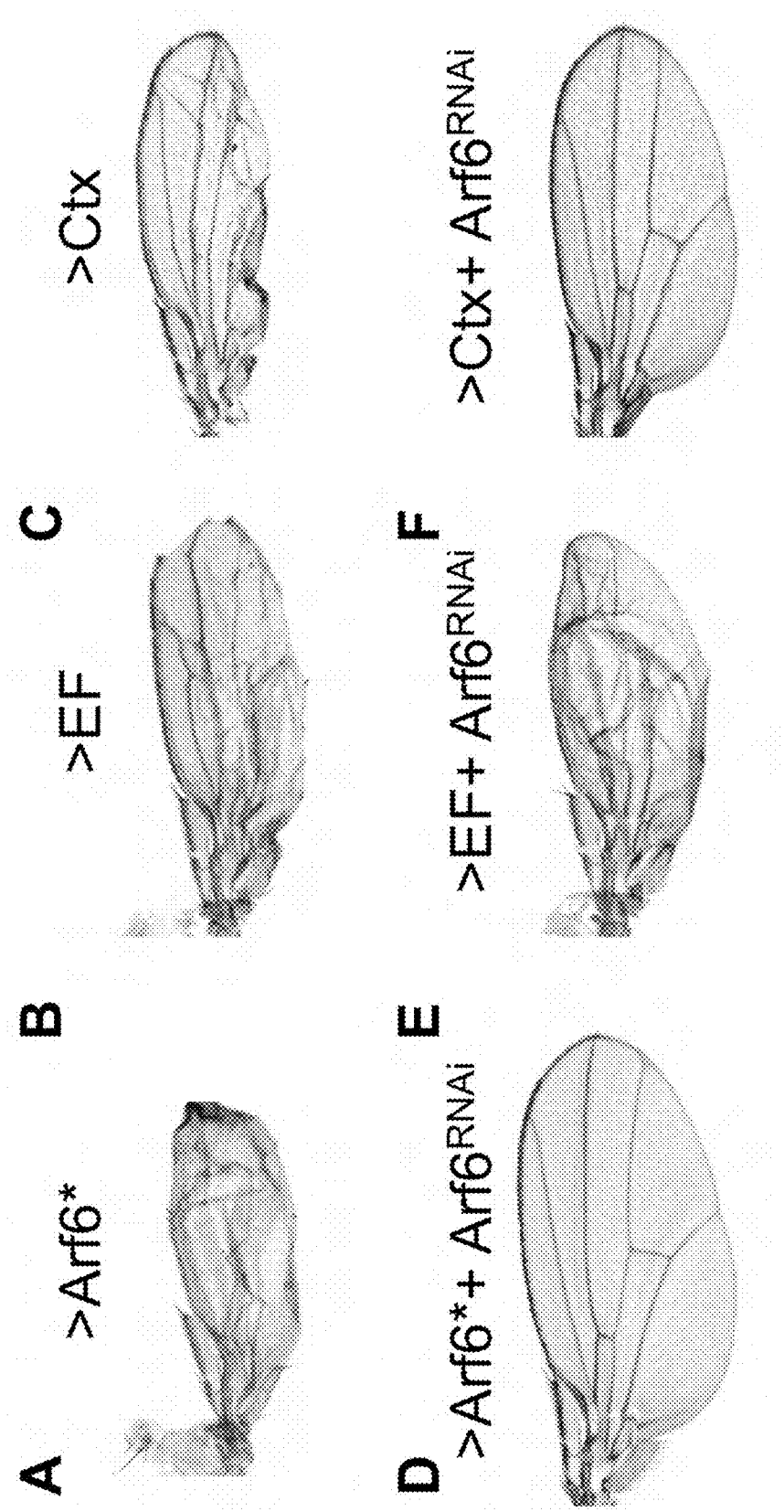
FIGS. 13A-13F show that Arf6RNAi suppresses the Ctx but not the EF phenotype. Wing phenotypes of the indicated genotype. wingGAL4=MS1096GAL4. Arf6*(FIG. 13A), EF (FIG. 13B), and Ctx (FIG. 13C) produce a similar phenotype in the wing. Co-expression with Arf6RNAi completely suppresses Arf6* phenotype (FIG. 13D), Arf6RNAi co-expression does not visibly alter the EF phenotype (FIG. 13E), but potently suppresses the Ctx phenotype (FIG. 13F).
Figures 14A, 14B, 14C, 14D, 14E, 14F:
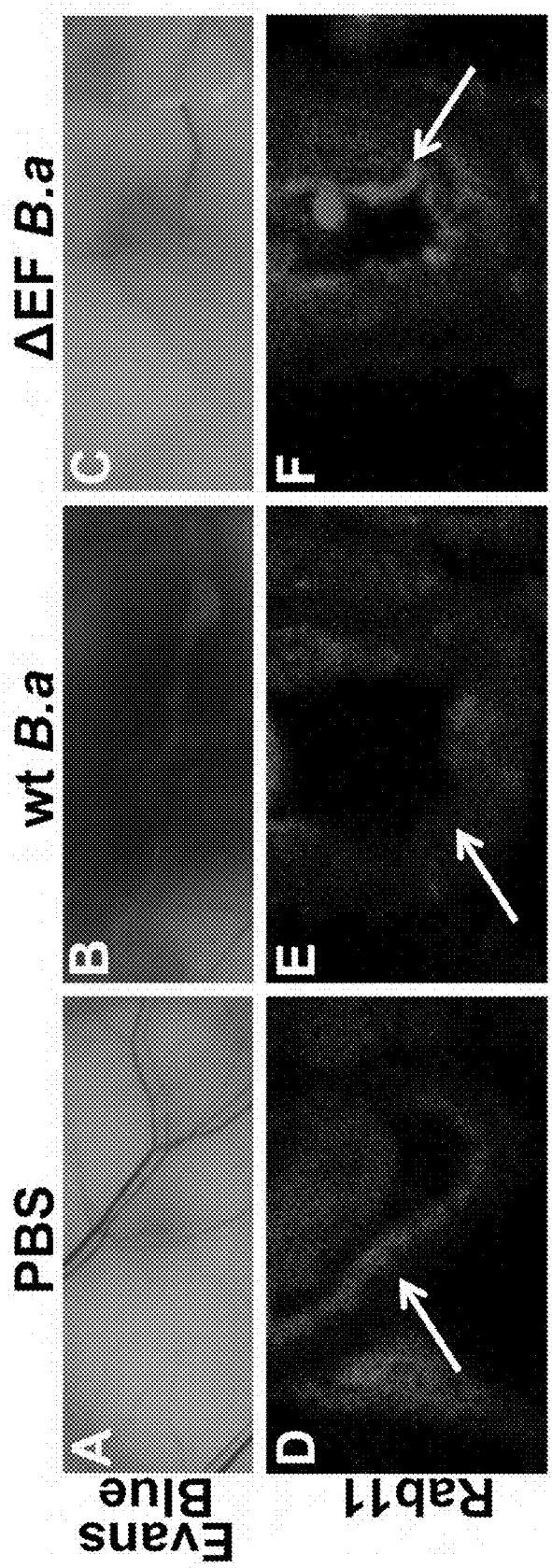
FIGS. 14A-14F shows that B.a infection causes a loss of luminal Rab11 in blood vessels.

Junctional homeostasis is also maintained by pathways controlling the retrieval of proteins via endocytic processes. Arf6, a small GTPase of the Arf subfamily (ADP-Ribosylation Factors) predominantly localizes to the plasma membrane and endosomes, and is involved in a variety of roles including early steps of endocytosis from the plasma membrane, exocytosis, and endosomal recycling [25]. Because Arf6 is known to contribute to sepsis by promoting vascular leakage through excessive internalization of VE-cadherins [40] and interacts with exocyst components [41], its potential role in mediating the phenotypes caused by cAMP-producing toxins in the system was examined. Strikingly, expression of an activated form of Arf6 (Arf6*) in the wing caused a phenotype nearly identical to that induced by EF (FIGS. 4A and 4B), consisting of small narrowed wings with thickened veins and blisters. In contrast, wild-type Arf6 (Arf6wt) expressed alone failed to cause any detectable phenotype (FIG. 4D). However, both wild-type and activated forms of Arf6 strongly enhanced the EF wing phenotype (FIGS. 4C and 4E). Further analysis revealed that Arf6* reduces the levels and apical restriction of Rab11 in the wing discs (FIGS. 4F and 4G), and inhibits the formation of the Sec15-rich structures (FIGS. 4H and 4I), in a manner similar to what was observed with the cAMP toxins EF and Ctx. Arf6* expression also reduced the levels of junctional D-Ecad (FIGS. 4J and 4K), as would be expected from its wing phenotype and effects on Rab11 and Sec15. Given the striking similarities between Arf6* and EF/Ctx phenotypes, whether Arf6 might mediate the effect of EF in the developing wing was tested, making use of an Arf6-RNAi construct that was highly effective in suppressing Arf6-dependent phenotypes (FIGS. 13A, 13D). Although Arf6-RNAi clearly suppressed the Ctx phenotype (S7C and S7F), it did not alter similar phenotypes induced by EF (FIGS. 13B, 13E). The suppression of Ctx phenotypes likely results from the known dependence of Ctx activation on Arf-GTPases, which act as cofactors for Ctx [42], although one cannot exclude the possibility that Arf6 may also mediate part of the downstream effects of Ctx. Whether Arf6* affects the behavior of Rab11* in salivary glands was also tested. As observed with EF and Ctx, Rab11* failed to concentrate as normal at the AJs in glands expressing Arf6* (FIGS. 4L and 4M), revealing that Arf6* similarly inhibits Rab11 at a step following GTP loading. In contrast to EF and Ctx, however, Arf6* induced an intracellular accumulation of Rab11, while also reducing Rab11 levels near the junctions (FIG. 4O), and caused striking accumulations of D-Ecad below the apical plasma membrane (FIGS. 4P and 4Q). Altogether, these observations suggest that the Arf6 pathway inhibits Rab11 activity, but most likely does so through a mechanism distinct from that of EF or Ctx.

Inhibitors of Either Arf6 or Epac Protect Against Effects of EF in Human Cells and In Vivo.

Because activation of PKA*, Rap1*, and Arf6* mimic features of the EF phenotype in Drosophila, the relative contribution of each of these pathways in EF-induced toxemia was examined in various experimental models relevant to B.a. infection in mammals. First, whether the distribution of Rab11 was affected by EF in tissues infected with wt-B.a. (Sterne strain) was tested. After intra-dermal injection (ID) of wt-B.a., mice develop skin edema that can be visualized through effusion of Evans Blue dye (EBD) [43]. This procedure was followed to compare the effects of ID injections with wt-B.a., AEF B.a. or a PBS control. After 6 hours, a positive control set of mice was injected with EBD to reveal EF-dependent edema (FIGS. 14A-14C). In the second set of similar mice, patches of skin surrounding the points of injection were processed for immuno-fluorescence. Staining of negative control skin patches revealed a luminal distribution of Rab11 in the blood vessels (FIG. 14D, arrow). In areas surrounding the wt-B.a. injection, however, this distribution of Rab11 was lost (FIG. 14E). In contrast, blood vessels surrounding the injection site of the mutant B.a. unable to produce ET (AEF-B.a.) displayed normalized Rab11 staining (FIG. 14F). It was concluded that, during B.a. infection, luminal targeting of Rab11 in blood vessels is blocked, an effect that depends primarily on EF, consistent with the current and previous [20] analyses.

The relative contributions of the Arf6, Epac, and PKA pathways to EF-induced inhibition of Rab11 was next examined, making use of HBMEC cultures. As was observed previously, ET treatment weakened AJs as revealed by an anti-pan-cadherin antibody (FIGS. 5A and 5B) [20]. To inhibit the Arf6 pathway, cells were treated with Slit2, a secreted peptide that activates the Robo4 receptor to promote vascular stability via stimulation of the ArfGAP GIT [27]. Cells co-treated with Slit2 appeared resistant to EF, as clearly illustrated by the re-establishment of junctional pan-cadherin accumulation (FIG. 5C). These findings suggest that Arf6 contributes to EF-induced inhibition of the Rab11/exocyst complex and weakening of AJs. Next, to determine the relative contribution of each branch of the cAMP pathway, EF-intoxicated cells were co-treated with ESI-09, an inhibitor specific for Epac [44], or with H89, a well-characterized inhibitor of PKA[45]. Surprisingly, it was found that only ESI-09 had the ability to partially restore normal junctional traffic and visible AJs (FIG. 5D), although junctions did not appear as regular as in untreated cells. In contrast H89 provided no detectable rescue to the EF-induced junctional phenotype (FIG. 5E). It was concluded that Epac/Rap1 is the predominant pathway mediating the cAMP induced effects of ET on exocyst-dependent junctional traffic in this setting.

To verify these conclusions in vivo, a footpad swelling assay was turned to in which intra-dermal injection of ET results in robust quantifiable edema [46]. In mice pretreated with SecinH3, a compound that inhibits the Arf6-GEF ARNO and thereby reduces Arf6 activity [27], ET-induced swelling was strongly inhibited (FIG. 5F). Indeed, in animals in which systemic pre-treatment with the drug induced observable symptoms of malaise indicative of drug efficacy, ET-induced edema was virtually abolished. The question of which branch(es) of the cAMP pathway contributed to EF-mediated edema was examined by comparing the relative abilities of H89 and ESI-09 to block ET-induced footpad swelling. Reinforcing the results of the cell experiments with HBMECs, it was found that while ESI-09 caused an absolute inhibition of edema, H89 had little or no effect (FIG. 5G). It was concluded that the Epac/Rap1 pathway is the primary mediator of EF-induced edema. In addition, the effect of AG1024 [47], an inhibitor of insulin-like growth factor receptor (IGF-1R) [48], was tested. Because IGF-1R has been shown to indirectly stimulate Rap1 [49], it was believed that inhibition of IGF-1R by AG1024 might conversely result in Rap1 inhibition. Indeed, pre-treatment of mice with AG1024 also led to significant reduction of edema, which was particularly strong at early time points (FIG. 5H). These findings, together with the results described above provide a framework for how effector pathways contribute to cAMP-mediated disruption of Rab11-dependent membrane trafficking (See FIG. 6 for summary diagram). In addition to a prominent role of the Epac/Rap1 branch in mediating the effect of ET, the study reveals a previously unappreciated form of negative cross-regulation between systems for the delivery and retrieval of membrane bound cargo, a feature that offers new therapeutic avenues for treating a range of diseases involving compromised integrity of epithelial or endothelial barriers.

Discussion

In previous studies, it was established that two cAMP toxins, EF from *Bacillus anthracis* [20] and Ctx from *Vibrio cholerae* [23], blocked Rab11-mediated endocytic recycling of cargo including signaling ligands and adhesion proteins (reviewed in [13,14]). However, the precise mechanisms by which cAMP overproduction interfered with Rab11-dependent trafficking remained to be established. Here, it was examined how cAMP effector pathways converge on discrete nodes of the trafficking process subsequent to the GTP loading step. In flies, this inhibition is mediated by both PKA and Epac/Rap1 effector pathways. PKA disrupts an early step in which Rab11 associates with endocytic membranes through a mechanism likely to involve phosphorylation of Rab11 effectors Rip11 and possibly Sec15. These events may entrain premature dissociation of Rab11/effector complexes. In contrast, Epac and Rap1 act a later step, when cargo-laden endosomes fuse with the plasma membrane (FIG. 6). The relative contribution of each cAMP response branch may vary in different systems. Thus in mammalian systems the Epac/Rap1 branch appears to be the primary effector of EF in blocking function of the Rab11/exocyst complex and inducing edema. It was also found that Arf6-mediated retrieval of junctional proteins acts in opposition to Rab11-mediated delivery by a mechanism that is similar to, but distinct from, that caused by cAMP toxins. These latter findings offer therapeutic avenues for alleviating cAMP-related toxemia by pharmacological inhibition of Arf6 or Epac, to reverse effects of cAMP inducing toxins or other barrier disruptive agents.

Activated PKA and Epac Pathways Disrupt Rab11-Dependent Trafficking after GTP Loading Typical of small GTPases, Rab11 cycles between active (GTP-bound) and inactive (GDP-bound) conformations, the former permitting interaction with effector proteins to carry out various downstream functions. Two types of regulators, GEFs and GAPs provide control for this essential cycle. In the particular case of Rab11, Crag (the sole *Drosophila* homolog of human DENND4A) is the only Rab11-dedicated GEF known at this time [30]. Similarly, only one Rab11-specific GAP has been identified: EVI5 [50,51,52]. None of these regulators contains a cAMP-binding domain that could provide a direct link between cAMP and upstream regulation of Rab11. Consistent with this inference, it was found that EF/Ctx act on Rab11 at a step subsequent to GTP loading. Indeed, transport of vesicles carrying the constitutively activated Rab11* is blocked by EF and Ctx, while total levels of Rab11-GTP do not appear to be greatly altered.

Dissection of PKA Versus Rap1 Effects on Rab11-Dependent Trafficking

The PKA-dependent Rab11 effector Rip11 is an attractive candidate for mediating a component of the effects of cAMP toxins as it contains a verified PKA phosphorylation site located in the central portion of the protein [38]. Indeed, PKA-dependent phosphorylation of Rip11 is required for cAMP-potentiated insulin secretion in pancreatic p-cells [38], and Ser/Thr phosphorylation has been shown to be responsible for Rip11 transition from the insoluble to cytosolic fraction in intestinal CACO-2 cells [53]. Although it was not determined whether this latter modification was specifically PKA-dependent, that study proposed a model in which phosphorylation of Rip11 is essential for cycling to a free state following interaction with Rab11 and specific membrane compartments and prior to its re-associating with Rab11. The data shows that the association of Rip11/Rab11—as well as Sec15/Rab11—can be abrogated by EF and PKA* in Drosophila and mammalian endothelial or kidney cells. Based on these experiments, it is proposed that unrelenting phosphorylation of Rip11 by PKA may cause the premature dissociation of Rab11 and its effectors, potentially leading to a failure to reach the AJs. While this PKA-dependent phosphorylation of Rip11 has been demonstrated in human pancreatic cells, it is not known whether it occurs in Drosophila. As dRip11 contains 19 candidate PKA phosphorylation sites, further investigation will help determine whether phosphorylation of one or more of these sites promotes the dissociation between dRip11 and Rab11. Intriguingly, Drosophila Sec15 also harbors several putative PKA phosphorylation sites, although such predicted sites are absent from its human counterpart.

The present model involving cyclic Rip11 association and dissociation with Rab11 could help explain the so-called "cAMP paradox" wherein low doses of cAMP are known to strengthen cell-cell junctions whereas higher non-physiological levels have the opposite pathological effect of destabilizing junctions. According to this model, low levels of cAMP may exert their positive effects on Rab11-dependent trafficking and maintenance of junctional integrity [38,54] by promoting the release of Rip11 from Rab11, which would be necessary for the final fusion event between recycling endosome and the plasma membrane. In contrast, high pathological cAMP concentrations may cause premature dissociation of the Rab11-Rip11 complex and permanently block that cycle. Because phosphorylation of RhoA by PKA is similarly known to inhibit its activation and to prevent increased endothelial permeability during inflammation [55], the interplay between RhoA and the exocyst downstream of PKA in EF-intoxicated cells also merits further examination.

The second branch of the cAMP pathway mediated by Rap1 and its cAMP-regulated GEF Epac [33] contributes significantly to the effect of EF in flies and appears to play the predominant role in mediating the effect of EF/Ctx in the mammalian systems examined. In flies, activated Rap1 (Rap1*) causes a wing phenotype similar to that of Rab11DN, and synergizes with PKA*. It was previously reported that Rap1* reduces the levels of Rab11 and prevents formation of Sec15 punctae [23]. In the present study, it was found that Rap1* does not prevent Rab11* from reaching the AJs, rather it alters its distribution, resulting in a double line flanking sites of cell-cell contact instead of the normal single sharp line observed when Rab11* is expressed alone. This suggests that the final exocyst- and SNARE-dependent fusion event with the apical plasma membrane can be blocked by exuberant Rap1* activity, leading to accumulation of non-functional Rab11* just beneath the plasma membrane. Consistent with this suggestion, Rap1 has been implicated by many studies in regulating of both cadherin and integrin-mediated cell-cell adhesion (reviewed in [56] [57]).

Among several known effectors of Rap1, the RalGEF Rgl1 (an activator of RalA) has been reported to bind to Rap1-GTP. Because lowering the dose of Rgl1, or expressing a Dominant-Negative form of RalA can suppress Rap1*-induced phenotypes in Drosophila, it has been proposed that RalA may act downstream of Rap1 [31]. Also, RalA is known to directly bind to exocyst components Sec5 [32] [58] [59] and Exo84 [60] and plays a central role in regulating exocyst-mediated processes in several settings, including the release of Von-Willebrand Factor from endothelial cells, or insulin secretion in pancreatic p-cells (reviewed in [56] and [61]). Thus, RalA over-activation appears as an attractive mechanism for mediating the effect of cAMP toxins on exocyst inhibition downstream of Rap1.

Previously, it was shown that inhibition of MAPK pathways by anthrax LF toxin synergizes with EF to inhibit exocyst function and most likely blocked exocyst-mediated vesicular docking down-stream of Rab11 [20]. The present studies suggest that blocking multiple steps through branching pathways that converge on critical nodes in endocytic recycling represents a successful strategy for pathogens to weaken host protective mechanisms relying on junctional integrity of epithelial and endothelial cell layers [24].

Integration of Membrane Trafficking Delivery and Retrieval Pathways

The small GTPase Arf6 is known to initiate retrieval of membrane proteins from cell junctions in a wide variety of cells types [25]. Arf6, a member of the ADP-ribosylation factor subfamily, is located at the plasma membrane and some endosomal compartments, and is involved in endocytosis from the plasma membrane, vesicular recycling, and exocytosis [62]. Importantly, Arf6 plays a role during sepsis to mediate acute VEGF-induced vascular permeability [40, 63]. Whether linchpin regulators of opposing vesicular trafficking pathways such as Arf6 and Rab11 interact had not yet been extensively explored. In this study, there is presented evidence that these trafficking systems do in fact engage in cross-inhibitory interactions. Consistent with the published role of Arf6 in promoting VE-cadherin endocytosis [64], it was found that the activated form of Arf6 (Arf6*) causes phenotypes similar to those of EF. The present findings suggest that the activity of Arf6 negatively feeds back on vesicular transport to the plasma membrane by reducing Rab11 function. Previous studies showed that Arf6 physically interacts with the exocyst component Sec10 [41], possibly contributing to the observed effect of Arf6 on Rab11 levels and distribution. Given the negative regulation of Rab11 by Arf6 in flies and its known role in compromising barrier function in the mammalian vasculature during sepsis [27,40], whether inhibitors of this pathway might act in part via Rab11 in these contexts was tested. In human cells, it was found indeed that treatment with Slit, a secreted peptide indirectly blocking the function of Arf6, could reverse the effects of EF, restoring formation of Sec15 punctae and junctional integrity in EF-treated HBMECs. Similarly, pharmacological inhibition of Arf6 by SecinH3, a compound that inhibits the ArfGEF Arno, blocked EF-induced edema in a mouse footpad assay. These latter findings along with the strong inhibition of footpad swelling by the Rap1 inhibitor ESI-09 suggest that a broad range of barrier disruptive diseases ranging from toxemia caused by cAMP-inducing toxins to inflammatory autoimmune diseases such as IBD and asthma that involve positive feedback loops between immune activation and barrier disruption could be treated with compounds that either inhibit Arf6 or Epac/Rap1 (such as those tested in this study), or by compounds that may boost Rab11 activity.

Materials and Methods

*Drosophila* Genetics:

UAS-EF and UAS-Ctx constructs and lines were described previously[20,23]. UAS-Rab11wt/TM3 (#9790), UAS-Rab11*(#9791), UAS-Rab11DN (#23261), and UAS-Arf6RNAi (#51417) lines were obtained from Bloomington *Drosophila* Stock Center (BDSC). UAS-Rap1*/TM6 and UAS-PKA*/CyO were generated by I. Hariharan (UCB), and D. Kalderon (Columbia University), respectively. UAS-RalARNAi was from VDRC (KK105296). UAS-Rip11GFP and UAS-Rip11DNGFP were kindly provided by Don Ready (Purdue University). UAS-Arf6* was generated in the Olson laboratory (UT Southwestern).

Immunological Stains of Wing Discs and Salivary Glands:

Imaginal discs were dissected, fixed and stained as described previously. Salivary glands were dissected similarly, fixed for 30 minutes, and left attached to carcasses until ready to mount in SlowFade (LifeTechnologies #S36936), using double sided tape as a spacer to prevent tissue squashing. Antibodies: rabbit anti-GFP antibody (1/500, ThermoFisher #A6455), rat-anti GFP antibody (1/500, SCBT #sc-101536), mouse anti-Rab11 (1/200, BD Biosciences #610657), mouse anti Rab11-GTP (1/100, NewEast Biosciences #26919) D-Ecad (1/500, DSHB #DCAD2). The rabbit anti-Rip11 (1/1000) was a gift from D. Ready (Purdue University) and A. Satoh (Hiroshima University, Japan), and guinea pig anti-Sec15 (1/1000) was kindly provided by Hugo Bellen (Baylor College of Medicine). Images were collected by confocal microscopy on a Leica TCS SP5.

Transient Expression of DsRed-Rab11A and Rip11-EGFP in MDCK Cells

MDCK cells (ATCC CCL-34) were maintained in DMEM (Corning; Manassas, Va.) containing 10% FBS, 1% Penicillin/streptomycin, 2 mM L-glutamine and were incubated in 37° C., 5% CO2 atmosphere. Cells were gently dislodged with 0.05% trypsin (Mediatech Inc.) and were electroporated with cDNA expressing DsRed-Rab11A (Addgene) and Rip11-EGFP (Kind gift from Dr. Rytis Prekeris, Univ. of Colorado at Denver) using Neon Transfection system (Life Technologies, Carlsbad, Calif.) according to manufacturers protocol. Briefly, cells were rinsed once with PBS and resuspended in buffer R at a density of $10^7$ cells/ml. cDNA expressing DsRed-Rab11 and Rip11-EGFP were added to the cell suspension, and cells were electroporated with a 10 gl Neon tip at 1650 V, 20 ms width and 1 pulse. The cells were immediately transferred to 600 gl pre-warmed DMEM containing 10% FBS, 1% Penicillin/streptomycin, 2 mM L-glutamine, of which 300 gl cell suspension was plated on each well of 8 chamber tissue culture treated glass slide (BD Falcon, Bedford, Mass.). Cells were treated with 10 ug/ml EF+20 ug/ml PA for 4 hrs before being fixed with 4% para-formaldehyde in PBS for 30 min at 37° C. and processed for imaging. Fluorescence images were collected using a Delta Vision RT microscope.

HBMEC Intoxications and Sec15GFP Transfections

HBMEC cultures were maintained in DMEM (Corning; Manassas, Va.) containing 10% FBS, 1% Penicillin/streptomycin, 2 mM L-glutamine and were incubated in 37° C., 5% CO2 atmosphere. Cells were gently dislodged with 0.05% trypsin (Mediatech Inc.) and cultured on glass poly-D-lysine coated chamber slides (BD Falcon #354108). At about 80% confluence, EF and PA (0.2 pg/ml-0.4 pg/ml) were added to cells. Drug co-treatments included: Slit2 (10 pg/ml, R&D systems #8616), ESI-09 (TOCRIS #4773, 100 pM), and H89 (TOCRIS #2910, 10 pM). After 24 hrs (FIGS. 5A-5H), cells were fixed for 10 mins at −20° C. in 100% Methanol, then washed with 0.1% Triton in PBS, Sec15GFP fluorescence was inspected directly, while Methanol-fixed cells were stained with a mouse anti pan-Cadherin antibody (Abcam, clone CH-19, 1/100). For FIGS. 12A-12F, cells were incubated with mouse anti Rab11-GTP (NewEast Bioscience #26919, 1/100). For FIGS. 12A-12F, transfection of the Sec15-GFP was performed with the FuGENE 9 transfection reagent (Roche) according to manufacturer recommendations. Cells were treated with ET (2 ug/ml EF/4 ug/ml PA), and fixed after 6 hrs of treatment for 30 mins in 4% PFA in PBS. Cells were stained with rabbit anti Rip11 (Novusbio #NBP1-81855, 1/500) and mouse anti Rab11-GTP (NewEast Bioscience #26919, 1/100) antibodies overnight at 4° C. Coverslips were washed, and incubated with secondary antibodies before mounting with Prolong Gold (ThermoFisher) with DAPI mounting media.

Intra-Dermal Infections in Mice

Nine-week-old CD-1 female mice were injected with 100 ml PBS control, or PBS containing $1 \times 10^6$ colony-forming units (c.f.u.) of *B. anthracis* Sterne, or AEF bacteria subcutaneously in the hind flank (three spots per mouse). After 6 h, half of the mice were injected intravenously with 0.1 ml of 2% Evans blue in PBS and killed 30 min later, for examination of leakage on inverted skin patches. Other mice were killed without Evans Blue injection, their skins were fixed overnight in 10% buffered Formalin, and paraffin-embedded. Sections were stained with a Rabbit anti Rab11 (Invitrogen #71-5300) after standard de-paraffinization procedure.

Mouse Footpad Edema Studies

BALB/cJ mice (8-10 weeks old, female; Jackson Laboratories, Bar Harbor, Me.) were intraperitoneally injected with drugs. SecinH3 (TOCRIS #2849), AG1024 (Selleckchem, S1234), ESI-09 (TOCRIS #4773) or H89 (TOCRIS #2910), or with vehicle (70% DMSO in isotonic glucose for SecinH3, 30% DMSO in isotonic glucose for other drugs) 2-3 h prior to injection of ET (0.15 pg/20 pl, right footpad) or PBS (20 pl, left footpad), and in the case of SecinH3, also 2 h post toxin injection. ESI-09, AG1024 and H89 were administered at 10 mg/kg and SecinH3 was administered as 250 ul and 2.5 mM solution. Edema was assessed at 8-10 h, or 18-24 h by dorsal/plantar measurements using digital calipers.

REFERENCES

1. McDonough K A, Rodriguez A (2011) The myriad roles of cyclic AMP in microbial pathogens: from signal to sword. Nat Rev Microbiol 10: 27-38.
2. Ahuja N, Kumar P, Bhatnagar R (2004) The adenylate cyclase toxins. Crit Rev Microbiol 30: 187-196.
3. Collier R J, Young J A (2003) Anthrax toxin. Annu Rev Cell Dev Biol 19: 45-70.
4. Young J A, Collier R J (2007) Anthrax toxin: receptor binding, internalization, pore formation, and translocation. Annu Rev Biochem 76: 243-265.
5. Tonello F, Montecucco C (2009) The anthrax lethal factor and its MAPK kinase-specific metalloprotease activity. Mol Aspects Med 30: 431-438.
6. Leppla S H (1982) Anthrax toxin edema factor: a bacterial adenylate cyclase that increases cyclic AMP concentrations of eukaryotic cells. Proc Natl Acad Sci USA 79: 3162-3166.

7. Tournier J N, Rossi Paccani S, Quesnel-Hellmann A, Baldari C T (2009) Anthrax toxins: a weapon to systematically dismantle the host immune defenses. Mol Aspects Med 30: 456-466.
8. Moayeri M, Leppla S H (2009) Cellular and systemic effects of anthrax lethal toxin and edema toxin. Mol Aspects Med 30: 439-455.
9. Rougeaux C, Becher F, Ezan E, Tournier J N, Goossens P L (2016) In vivo dynamics of active edema and lethal factors during anthrax. Sci Rep 6: 23346.
10. Frankel A E, Kuo S R, Dostal D, Watson L, Duesbery N S, et al. (2009) Pathophysiology of anthrax. Front Biosci (Landmark Ed) 14: 4516-4524.
11. Guichard A, Nizet V, Bier E (2012) New insights into the biological effects of anthrax toxins: linking cellular to organismal responses. Microbes Infect 14: 97-118.
12. Guichard A, Park J M, Cruz-Moreno B, Karin M, Bier E (2006) Anthrax lethal factor and edema factor act on conserved targets in Drosophila. Proc Natl Acad Sci USA 103: 3244-3249.
13. Welz T, Wellbourne-Wood J, Kerkhoff E (2014) Orchestration of cell surface proteins by Rab11. Trends Cell Biol 24: 407-415.
14. Kelly E E, Horgan C P, McCaffrey M W (2012) Rab11 proteins in health and disease. Biochem Soc Trans 40: 1360-1367.
15. Langevin J, Morgan M J, Sibarita J B, Aresta S, Murthy M, et al. (2005) Drosophila exocyst components Sec5, Sec6, and Sec15 regulate DE-Cadherin trafficking from recycling endosomes to the plasma membrane. Dev Cell 9: 365-376.
16. Jafar-Nejad H, Andrews H K, Acar M, Bayat V, Wirtz-Peitz F, et al. (2005) Sec15, a component of the exocyst, promotes notch signaling during the asymmetric division of Drosophila sensory organ precursors. Dev Cell 9: 351-363.
17. Zhang X M, Ellis S, Sriratana A, Mitchell C A, Rowe T (2004) Sec15 is an effector for the Rab11 GTPase in mammalian cells. J Biol Chem 279: 43027-43034.
18. Wu S, Mehta S Q, Pichaud F, Bellen H J, Quiocho F A (2005) Sec15 interacts with Rab11 via a novel domain and affects Rab11 localization in vivo. Nat Struct Mol Biol 12: 879-885.
19. Martin-Urdiroz M, Deeks M J, Horton C G, Dawe H R, Jourdain I The Exocyst Complex in Health and Disease. Front Cell Dev Biol 4: 24.
20. Guichard A, McGillivray S M, Cruz-Moreno B, van Sorge N M, Nizet V, et al. (2010) Anthrax toxins cooperatively inhibit endocytic recycling by the Rab11/Sec15 exocyst. Nature 467: 854-858.
21. Sack D A, Sack R B, Nair G B, Siddique A K (2004) Cholera. Lancet 363: 223-233.
22. Sanchez J, Holmgren J (2011) Cholera toxin—a foe & a friend. Indian J Med Res 133: 153-163.
23. Guichard A, Cruz-Moreno B, Aguilar B, van Sorge N M, Kuang J, et al. (2013) Cholera toxin disrupts barrier function by inhibiting exocyst-mediated trafficking of host proteins to intestinal cell junctions. Cell Host Microbe 14: 294-305.
24. Guichard A, Nizet V, Bier E (2014) RAB11-mediated trafficking in host-pathogen interactions. Nat Rev Microbiol 12: 624-634.
25. Hongu T, Kanaho Y (2013) Activation machinery of the small GTPase Arf6. Adv Biol Regul 54: 59-66.
26. Hafner M, Schmitz A, Grune I, Srivatsan S G, Paul B, et al. (2006) Inhibition of cytohesins by SecinH3 leads to hepatic insulin resistance. Nature 444: 941-944.
27. Jones C A, Nishiya N, London N R, Zhu W, Sorensen L K, et al. (2009) Slit2-Robo4 signalling promotes vascular stability by blocking Arf6 activity. Nat Cell Biol 11: 1325-1331.
28. Zhang J, Schulze K L, Hiesinger P R, Suyama K, Wang S, et al. (2007) Thirty-one flavors of Drosophila rab proteins. Genetics 176: 1307-1322.
29. Farkas R, Benova-Liszekova D, Mentelova L, Mahmood S, Datkova Z, et al. (2015) Vacuole dynamics in the salivary glands of Drosophila melanogaster during pre-pupal development. Dev Growth Differ 57: 74-96.
30. Xiong B, Bayat V, Jaiswal M, Zhang K, Sandoval H, et al. (2012) Crag is a GEF for Rab11 required for rhodopsin trafficking and maintenance of adult photoreceptor cells. PLoS Biol 10: e1001438.
31. Mirey G, Balakireva M, L'Hoste S, Rosse C, Voegeling S, et al. (2003) A Ral guanine exchange factor-Ral pathway is conserved in Drosophila melanogaster and sheds new light on the connectivity of the Ral, Ras, and Rap pathways. Mol Cell Biol 23: 1112-1124.
32. Moskalenko S, Henry D O, Rosse C, Mirey G, Camonis J H, et al. (2002) The exocyst is a Ral effector complex. Nat Cell Biol 4: 66-72.
33. de Rooij J, Zwartkruis F J, Verheijen M H, Cool R H, Nijman S M, et al. (1998) Epac is a Rap1 guanine-nucleotide-exchange factor directly activated by cyclic AMP. Nature 396: 474-477.
34. Roberts O L, Dart C (2014) cAMP signalling in the vasculature: the role of Epac (exchange protein directly activated by cAMP). Biochem Soc Trans 42: 89-97.
35. Li W, Ohlmeyer J T, Lane M E, Kalderon D (1995) Function of protein kinase A in hedgehog signal transduction and Drosophila imaginal disc development. Cell 80: 553-562.
36. Horgan C P, McCaffrey M W (2009) The dynamic Rab11-FIPs. Biochem Soc Trans 37: 1032-1036.
37. Li B X, Satoh A K, Ready D F (2007) Myosin V, Rab11, and dRip11 direct apical secretion and cellular morphogenesis in developing Drosophila photoreceptors. J Cell Biol 177: 659-669.
38. Sugawara K, Shibasaki T, Mizoguchi A, Saito T, Seino S (2009) Rab11 and its effector Rip11 participate in regulation of insulin granule exocytosis. Genes Cells 14: 445-456.
39. Desclozeaux M, Venturato J, Wylie F G, Kay J G, Joseph S R, et al. (2008) Active Rab11 and functional recycling endosome are required for E-cadherin trafficking and lumen formation during epithelial morphogenesis. Am J Physiol Cell Physiol 295: C545-556.
40. Davis C T, Zhu W, Gibson C C, Bowman-Kirigin J A, Sorensen L, et al. (2014) ARF6 inhibition stabilizes the vasculature and enhances survival during endotoxic shock. J Immunol 192: 6045-6052.
41. Prigent M, Dubois T, Raposo G, Derrien V, Tenza D, et al. (2003) ARF6 controls post-endocytic recycling through its downstream exocyst complex effector. J Cell Biol 163: 1111-1121.
42. O'Neal C J, Jobling M G, Holmes R K, Hol W G (2005) Structural basis for the activation of cholera toxin by human ARF6-GTP. Science 309: 1093-1096.
43. Radu M, Chernoff J (2013) An in vivo assay to test blood vessel permeability. J Vis Exp: e50062.
44. Zhu Y, Chen H, Boulton S, Mei F, Ye N, et al. (2015) Biochemical and pharmacological characterizations of ESI-09 based Epac inhibitors: defining the ESI-09 "therapeutic window". Sci Rep 5: 9344.

45. Lochner A, Moolman J A (2006) The many faces of H89: a review. Cardiovasc Drug Rev 24: 261-274.
46. Zhao T, Zhao X, Liu J, Meng Y, Feng Y, et al. (2016) Diminished but Not Abolished Effect of Two His351 Mutants of Anthrax Edema Factor in a Murine Model. Toxins (Basel) 8: 35.
47. Wen B, Deutsch E, Marangoni E, Frascona V, Maggiorella L, et al. (2001) Tyrphostin AG 1024 modulates radiosensitivity in human breast cancer cells. Br J Cancer 85: 2017-2021.
48. Bouallegue A, Vardatsikos G, Srivastava A K (2009) Role of insulin-like growth factor 1 receptor and c-Src in endothelin-1- and angiotensin II-induced PKB phosphorylation, and hypertrophic and proliferative responses in vascular smooth muscle cells. Can J Physiol Pharmacol 87: 1009-1018.
49. Van Kolen K, Gilany K, Moens L, Esmans E L, Slegers H (2006) P2Y12 receptor signalling towards PKB proceeds through IGF-I receptor cross-talk and requires activation of Src, Pyk2 and Rap1. Cell Signal 18: 1169-1181.
50. Dabbeekeh J T, Faitar S L, Dufresne C P, Cowell J K (2007) The EVI5 TBC domain provides the GTPase-activating protein motif for RAB11. Oncogene 26: 2804-2808.
51. Laflamme C, Assaker G, Ramel D, Dorn J F, She D, et al. (2012) Evi5 promotes collective cell migration through its Rab-GAP activity. J Cell Biol 198: 57-67.
52. Laflamme C, Emery G (2015) In vitro and in vivo characterization of the Rab11-GAP activity of *Drosophila* Evi5. Methods Mol Biol 1298: 187-194.
53. Prekeris R, Klumperman J, Scheller R H (2000) A Rab11/Rip11 protein complex regulates apical membrane trafficking via recycling endosomes. Mol Cell 6: 1437-
54. Park S W, Schonhoff C M, Webster C R, Anwer M S (2014) Rab11, but not Rab4, facilitates cyclic AMP- and tauroursodeoxycholate-induced MRP2 translocation to the plasma membrane. Am J Physiol Gastrointest Liver Physiol 307: G863-870.
55. Qiao J, Huang F, Lum H (2003) PKA inhibits RhoA activation: a protection mechanism against endothelial barrier dysfunction. Am J Physiol Lung Cell Mol Physiol 284: L972-980.
56. Boettner B, Van Aelst L (2009) Control of cell adhesion dynamics by Rap1 signaling. Curr Opin Cell Biol 21: 684-693.
57. Frische E W, Zwartkruis F J (2010) Rap1, a mercenary among the Ras-like GTPases. Dev Biol 340: 1-9.
58. Fukai S, Matern H T, Jagath J R, Scheller R H, Brunger A T (2003) Structural basis of the interaction between RalA and Sec5, a subunit of the sec6/8 complex. EMBO J 22: 3267-3278.
59. Wang L, Li G, Sugita S (2004) RalA-exocyst interaction mediates GTP-dependent exocytosis. J Biol Chem 279: 19875-19881.
60. Jin R, Junutula J R, Matern H T, Ervin K E, Scheller R H, et al. (2005) Exo84 and Sec5 are competitive regulatory Sec6/8 effectors to the RalA GTPase. EMBO J 24: 2064-2074.
61. Shirakawa R, Horiuchi H (2015) Ral GTPases: crucial mediators of exocytosis and tumourigenesis. J Biochem 157: 285-299.
62. D'Souza-Schorey C, Chavrier P (2006) ARF proteins: roles in membrane traffic and beyond. Nat Rev Mol Cell Biol 7: 347-358.
63. Ikeda S, Ushio-Fukai M, Zuo L, Tojo T, Dikalov S, et al. (2005) Novel role of ARF6 in vascular endothelial growth factor-induced signaling and angiogenesis. Circ Res 96: 467-475.
64. Gavard J, Gutkind J S (2006) VEGF controls endothelial-cell permeability by promoting the beta-arrestin-dependent endocytosis of VE-cadherin. Nat Cell Biol 8: 1223-1234.

The invention claimed is:

1. A method for reducing inflammation due to edema toxin, comprising administering to a mammalian subject in need thereof an effective amount of a composition comprising ESI-09.

2. The method of claim 1, wherein the subject is a human.

3. The method of claim 1, wherein the composition preserves, restores, or both, epithelial barrier integrity, endothelial barrier integrity, or both.

4. The method of claim 1, wherein the composition is administered as part of an oral rehydration formula or an IV fluid.

5. A method for reducing inflammation due to edema toxin, comprising administering to a mammalian subject in need thereof an effective amount of a composition comprising AGT1024.

6. The method of claim 5, wherein the subject is a human.

7. The method of claim 5 wherein the composition preserves, restores, or both, epithelial barrier integrity, endothelial barrier integrity, or both.

8. The method of claim 5, wherein the composition is administered as part of an oral rehydration formula or an IV fluid.

9. A method for reducing inflammation due to edema toxin, comprising administering to a mammalian subject in need thereof an effective amount of a composition comprising SecinH3.

10. The method of claim 9, wherein the subject is a human.

11. The method of claim 9, wherein the composition preserves, restores, or both, epithelial barrier integrity, endothelial barrier integrity, or both.

12. The method of claim 9, wherein the composition is administered as part of an oral rehydration formula or an IV fluid.

13. A method for reducing inflammation due to edema toxin, comprising administering to a mammalian subject in need thereof an effective amount of a composition comprising Slit2.

14. The method of claim 13, wherein the subject is a human.

15. The method of claim 13, wherein the composition preserves, restores, or both, epithelial barrier integrity, endothelial barrier integrity, or both.

16. The method of claim 13, wherein the composition is administered as part of an oral rehydration formula or an IV fluid.

* * * * *